US009417193B2

(12) United States Patent
Globus et al.

(10) Patent No.: US 9,417,193 B2
(45) Date of Patent: Aug. 16, 2016

(54) TERAHERTZ SPECTROSCOPY CHARACTERIZATION WITH HIGH SPECTRAL AND SPATIAL RESOLUTION FOR BIOLOGICAL AND CHEMICAL SENSING AND METHOD OF USE

(71) Applicants: Tatiana Globus, Charlottesville, VA (US); Aaron Moyer, Ruckersville, VA (US); Jerome Ferrance, Charlottesville, VA (US); Boris Gelmont, Charlottesville, VA (US)

(72) Inventors: Tatiana Globus, Charlottesville, VA (US); Aaron Moyer, Ruckersville, VA (US); Jerome Ferrance, Charlottesville, VA (US); Boris Gelmont, Charlottesville, VA (US)

( * ) Notice: Subject to any disclaimer, the term of this patent is extended or adjusted under 35 U.S.C. 154(b) by 48 days.

(21) Appl. No.: 13/957,395

(22) Filed: Aug. 1, 2013

(65) Prior Publication Data

US 2014/0070102 A1 Mar. 13, 2014

Related U.S. Application Data

(60) Provisional application No. 61/678,229, filed on Aug. 1, 2012.

(51) Int. Cl.
*G01N 22/00* (2006.01)
*G01N 21/3586* (2014.01)

(52) U.S. Cl.
CPC ............ *G01N 22/00* (2013.01); *G01N 21/3586* (2013.01)

(58) Field of Classification Search
CPC ........................... G01N 22/00; G01N 21/3586
See application file for complete search history.

(56) References Cited

U.S. PATENT DOCUMENTS

| 7,675,037 | B2 | 3/2010 | Li et al. | |
| 8,748,822 | B1* | 6/2014 | Gerecht et al. | 250/339.07 |
| 2008/0014580 | A1 | 1/2008 | Alfano et al. | |
| 2010/0102233 | A1* | 4/2010 | Gelmond | 250/341.1 |
| 2014/0008540 | A1 | 1/2014 | Yasuda et al. | |

* cited by examiner

*Primary Examiner* — David Porta
*Assistant Examiner* — Mindy Vu
(74) *Attorney, Agent, or Firm* — Dale Jensen, PLC; Dale Jensen

(57) ABSTRACT

Biological cells or spores are analyzed by using enhanced THz coupling to molecules by depositing a test material in a channel of a microfluidic chip using near field sensing of sub-THz radiation from the molecules. The THz radiation is enhanced by transmitting THz radiation through slots in the chip, illuminating molecules of the test material with the enhanced THz radiation transmitted through the slots. A spectroscopic signature of the test material is generated, and a database of signatures of materials is generated. The test material is identified by comparing the signature of the test material with signatures of materials in the database.

16 Claims, 24 Drawing Sheets

Fig. 5. Periodicity of a THz signal in the direction perpendicular to the channels (in gray).

Highly resolved absorption spectra from *E. coli* non-pathogenic strain BL21, and deadly strain EDL933 (O157:H7), 60 bp models, water box 12 Å, averaged in all three directions, dissipation factor 0.12 $cm^{-1}$.

THz absorption spectra of two *E. coli* strains, pathogenic CFT073 and non-pathogenic BL21. 60 bp models, six matrices, water box 12 Å. Dissipation factor is $0.5$ $cm^{-1}$ for a moderate spectral resolution of $0.25$ $cm^{-1}$ (Bruker FTIR).

Figure 21. Difference in signatures from two lines of ovarian cancer cells

TERAHERTZ SPECTROSCOPY CHARACTERIZATION WITH HIGH SPECTRAL AND SPATIAL RESOLUTION FOR BIOLOGICAL AND CHEMICAL SENSING AND METHOD OF USE

STATEMENT REGARDING FEDERALLY-SPONSORED RESEARCH OR DEVELOPMENT

US Army Research Office SBIR Phase II, 14 May 2008_13 May 2010, Proposal Number: 54175ELCB2, Contract Number: W911NF-08-C-0049.

Defense Threat Reduction Agency, grant #HDTRA1-08-1-0038 and by the contract from the ARO #W911NF-08-C-0049.

FIELD OF THE INVENTION

A device and method of terahertz spectroscopy characterization for biological/chemical sensing in liquid and solid states with high spectral and spatial resolution.

DESCRIPTION OF THE INVENTION

Terahertz (THz) vibrational spectroscopy is relatively new technique that is a fast emerging for detection, characterization and identification of large macromolecules and organisms. This technique can be more effective than standard methods especially when the quantity of sample material is limited. Emerging highly resolved THz vibrational spectroscopy is an optical, label and reagent free technique that has now been found to be capable of being used to examine, detect, and identify bacterial cells to the level of strains.

THz radiation interacts with low-frequency internal molecular vibrations by exciting these vibrations, most of which are due to the torsion angle variations that produce collective motions of many atoms in concert. It is based on the specificity of spectroscopic signature at characteristic resonance frequencies. The capability of THz spectroscopy to detect directly low-frequency vibrations of weakest bonds between groups of atoms within biological molecules is unique providing the information quite different from the visible or infrared spectroscopic characterization. Implementation of terahertz spectroscopic and imaging technology in integrated Lab-on-a-Chip THz sensors with a sub-wavelength spatial resolution provides the opportunity to detect and image biomolecules at monolayer thickness in the aqueous environment, and in a near real-time.

These motions involve molecular groupings connected by the weakest bonds: weak hydrogen bonds, van der Waals and hydrophobic interactions. The resonant frequencies of such motions, vibrational modes, that usually occur below 300 $cm^{-1}$ (9 THz), are strongly dependent on a three-dimensional molecular structure and in particular on weak intra-molecular hydrogen bonding and non-bonded interactions between different functional groups. As such these vibrational modes are sensitive to conformational changes of molecules and to the environment. The THz region of absorption spectra for bio-molecules and species reveals these low frequency molecular motions. Each type of bio molecules possesses its unique resonant absorption characteristics, a THz fingerprint. Thus, THz vibrational spectroscopy techniques for identification are based on the specificity of a spectroscopic signature at characteristic resonance frequencies. At the same time, this technique is non-destructive for living species, with identification based on specific resonance features, vibrational modes or group of modes at close frequencies, in absorption (transmission) spectra of large biological molecules or whole bacterial cells/spores.

The capability of THz spectroscopy to directly detect low-energy vibrations of the weakest bonds, including hydrogen bonds, is unique, providing information quite different from visible or IR spectroscopic characterization. Although hydrogen bonds are weak and have only ~5% of the strength of covalent bonds, multiple hydrogen bonds stabilize the structure of bio-polymers, in particular holding the two strands of the DNA double helix together, or stabilizing polypeptides secondary structure conformations. The subTHz/THz regions of experimental absorption spectra of bio-molecules and species reveal these low frequency molecular motions.

THz signatures of large macromolecules and organisms occur in the sub-THz range starting from much lower frequencies of 30-50 GHz. The spectral range below 1 THz has been found to be the most attractive for practical applications because of low disturbance from absorption by water vapors in air or liquid water or from other analytes.

Terahertz spectroscopy systems use radiation to extract molecular spectral information in an otherwise inaccessible portion of the electromagnetic spectrum. Time domain spectroscopy and a photomixing technology, are also used for THz characterization of biological and organic materials. There have been however a very limited number of absorption (or transmission) spectroscopic studies in the submillimeter-wave regime due to the unique experimental difficulties that are presented there. In this region between the microwave (~0.1 THz) and the lower end of the far IR (~1 THz), the output power of the available sources is limited while the absolute absorption of the biological material is relatively weak. Time domain spectroscopy does not have adequate spectral resolution, and photomixing technology can provide only very low power.

The latest and most convincing THz-frequency spectroscopic results for biological materials have been obtained from Fourier Transform Infrared (FTIR) studies. The correct choice of substrate, the concentration of material in solution or suspension, and material alignment at deposition enabled significant enhancement of the intensities of modes and the reproducibility of frequencies when using a broadband commercial spectrometer, such as a FT Bruker IFS66v spectrometer, equipped with a detector operating at 1.7 K with a moderate spectral resolution of 0.25 $cm^{-1}$. Not only were raw transmission spectra able to be measured, it was also possible to extract absorption coefficient data for quantitative characterization of bio-materials. Bacteria are very complex biological objects. Their small size and relatively low absorption coefficient means THz radiation propagates through the entire object, allowing the genetic material and proteins to contribute to the THz signature of individual bacteria or spores. Transmission/absorption spectra measured with this FT spectrometer, equipped with a detector operating at 1.7° K. are rich in well resolved features having spectral widths of ~0.5-1 $cm^{-1}$. Molecular dynamic (MD) simulations for relatively small molecular components correlate rather well with the experimental data. Experimental results and their analysis have confirmed that observed spectroscopic features from biological cells/spores are caused by fundamental physical mechanism of interaction between THz radiation and biological macro-molecules. Particularly, the analysis of results indicates that the spectroscopic signatures of microorganisms originate from the combination of low energy vibrational modes or group of modes at close frequencies (vibrational bands) within molecular components of the bacterial cells/spores, with a significant contribution from the DNA.

There has been a widespread concern, as discussed in E. J. Heilweil & D. F. Plusquelic, "Terahertz Spectroscopy of Biomolecules" Terahertz Spectroscopy, Ch. 7, pp. 269-297, CRC Press, Taylor & Francis Group, LLC, London, N. York, 2008, that a large density of overlapping states contributing to the absorption bands of macromolecules might obscure vibrational resonances and yield essentially structureless spectra. This skepticism can be argued due to the fact that vibrational bands in spectra of, for example, proteins are observed and very well studied in the far IR region at much higher densities of states compared to THz. It was also demonstrated by others that not only biopolymers but whole microorganisms can be characterized in the IR and THz ranges. Multiple resonances due to low energy vibrational modes within biological macromolecules and bio-cells have been unambiguously demonstrated experimentally in the sub-THz frequency range in agreement with theoretical predictions.

It has now been found that the benefits from sub-THz characterization can be based on broad potential dual applications of vibrational spectroscopy of microorganisms, in conjunction with the generation of a database, which will provide for rapid detection and identification of bio threat and environmental agents, food quality and water contamination control, and disease diagnosis and therapy. THz molecular recognition signatures that are complimentary to those present in IR and UV spectra pave the way for development of sensitive optical biosensors with increased discrimination of biological threats and in more varied environments. Combined simulated and experimental results enable the finding of the optimal sub-range with the maximum number of the most intense absorption lines to build spectroscopic sensors with the best detection and discriminative capabilities.

The spectral resolution of the Bruker spectrometer (0.25 cm$^{-1}$) does not provide good discriminative capability. The spectral width of individual spectral lines (vibrational modes) and the intensity of absorption resonance features observed in sub-THz spectroscopy are sensitive to the relaxation processes of atomic dynamics (displacements) within a macromolecule that are not yet completely understood. These processes thus determine the discriminative capability of sub-THz spectroscopy. There is, however, evidence that multiple relaxation processes coexist in the low energy vibrational movements including long-living vibrations. These processes determine the life time scales and spectral resonances of DNA and proteins in the sub-THz/THz frequency range. Although, the entire mechanism of molecular dynamics is still not understood and needs to be studied, the suggested range of molecular dynamics relaxation times ($\tau$) for processes without biomolecular conformational change is varying from approximately 650 ps to 1.5 ps in different studies. The corresponding values for the dissipation factor $\gamma$ and the width of spectral lines, which are reciprocal to ($\tau$) are between 0.05 and 20 cm$^{-1}$. Values of $\gamma$ above 1 cm$^{-1}$ would result in structure-less sub-THz spectra, since vibrational resonances could not be resolved in this case because of the large density of low intensity vibrational modes.

The experimental results from measurements with high spectral resolution have already demonstrated very intense and narrow spectral features from biological molecules and bacteria with widths between 0.05 and 0.2 cm-1. These features were not evident in previous results using a resolution of 0.25 cm-1. The analysis of the results also suggested the coexistence of diverse relaxation dynamics mechanisms relevant to the sub-THz frequency region.

Further improvements in sensitivity and especially the discriminative capability of sub-THz vibrational spectroscopy for detection, characterization, and identification of bacterial organisms requires spectral resolution adequate to the width of spectral features.

Using a continuous-wave, frequency-domain spectroscopic sensor sub-THz characterization with improved spectral resolution has become possible with the sensor having imaging capability operating at room temperature in the sub-THz spectral region between 315 and 480 GHz as disclosed in, "A new method of local electro-magnetic field enhancement of Terahertz (THz) radiation in sub-wavelength regions with increased radiation coupling to biomaterials through the use of the discontinuity edge effect," U.S. Pat. No. 8,309,930, issued Nov. 13, 2012.

One of the intriguing qualities of terahertz radiation is that it can excite the low-frequency molecular vibrations produced by groups of atoms in biomolecules. Because each type of biomolecule produces its own vibrational signature, terahertz excitation can be used to identify unknown molecules.

SUMMARY OF THE INVENTION

An aspect of the invention relates to highly sensitive frequency domain resonance spectroscopy with high spectral and spatial resolution for characterizing ultra-small amounts of materials (at the level of ~1 ng or less) that have active absorption modes at frequencies from 4-40 cm$^{-1}$. The spectroscopy system comprises a THz source of radiation and a micro-detector with a microcircuit, both suitable for operation somewhere within this range, a motorized, or mechanical, stage for holding a micro/nanofluidic chip for a sample material, and a three-dimensional positioning of the components with an accuracy better than 1μ. Integrated as part of this system are a micro/nanofluidic chip platform with a manifold for precise positioning of a sample material using electrophoretic or other mechanism of liquid movement, a plasmonic device to effectively couple radiation passed through the sample and deliver this radiation into the detector waveguide, a high resolution optical visualization system to control the positioning. Computer controlled hardware and software enable reproducible and accurate positioning of components and data acquisition: signal vs. frequency, time, and three-position coordinates.

The present invention relates to a method of analyzing biological cells or spores using enhanced THz coupling to molecules. The method comprises the steps of: depositing a test material near a member selected from the group comprising doped semiconductors, metal films, and multilayer structures, the member being characterized by supporting modes that locally enhance EM fields, and near field sensing of THz radiation from the molecules, enhancing the THz radiation by transmitting THz radiation through slots in the member, illuminating molecules of the test material with the enhanced THz radiation transmitted through the slots, generating a spectroscopic signature of the test material, generating a database of signatures of materials, and identifying the test material by comparing the signature of the test material with signatures of materials in the database.

In addition, the enhanced THz radiation can be an EM field of terahertz radiation in a submicron region and further comprising the step of analyzing the THz vibration absorption by the test material and thereby generating the signature for the test material. In addition, the test material can comprise a strain of *E coli* and the database comprises signatures of pathogenic and non-pathogenic strains of *E coli*, and the method further comprises the step of comparing the signature of the test material with signatures of pathogenic and nonpathogenic strains of *E coli*, and determining whether the test material is a pathogenic strain of *E coli*, or a non-pathogenic strain of *E coli*.

In addition, the test material can comprise a cancer cell and further comprises the step of identifying a single cancer cell by interrogation of specific resonances caused by intra-molecular motions within the cell, and includes at least one of the steps of detection of signaling molecules circulating in blood and assessing therapeutic responses from cancer cells. In addition, the method can include the step of near field scanning with a THz antenna, of transmitted radiation of a slotted member from sample material near discontinuity edges of the slotted member.

In addition, the method can include the transmitting of THz radiation through the slots to increase the degree of the coupling of EM radiation in the THz spectral range to materials of interest by transmitting THz radiation through an array of openings, transmitting the THz radiation from the array of openings through bio- or chemical material and sensing near field THz radiation that has been transmitted through the slots and the material, and further comprising detection of the spectroscopic signatures of the bio- or chemical material.

Another embodiment of the invention relates to a method of increasing coupling of EM radiation in the THz spectral range to weak bonds in molecules using a spectroscopic instrument, the spectroscopic instrument having a chip, the chip having at least one micro or nano fluidic channel comprising the steps of depositing a material in a channel in a the chip, positioning a non-contact probe within a distance of 2-10 μm of the chip, and further comprises the steps of generating THz radiation, transmitting THz radiation through the material, and illuminating the material with the transmitted THz radiation, generating EM field enhancement at the microfluidic chip, selectively detecting enhanced THz transmitted through the material, monitoring the selectively detected enhanced THz radiation, and determining the spectroscopic signature of the material.

In addition, the material can be a bio-material in a biophysical process, and the method can further comprise monitoring at room temperature in at least near real-time changes of a dielectric property of the bio-material in a biophysical process in at least near real-time, wherein the process is selected from the group comprising denaturation of DNA, folding-unfolding of proteins, and structural conformational changes of biomolecules in interactions with drugs.

Another embodiment of the invention relates to an all-optical, apertureless continuous-wave frequency-domain spectroscopic sensor instrument free of mechanical tips or probes to contact testing material. The instrument can further include: a microfluidic chip, a source of sub-THz radiation, an analyte material in a channel of the microfluidic chip, means for illuminating the analyte material with the sub-THz radiation, and means to sense near field sub-THz radiation in the sub-THz spectral region between 315 and 480 GHz, from the analyte material. In addition, the analyte material can be a nano-gram sample of a biological material.

The spectroscopic sensor instrument can further include a non-contact probe, means for positioning the non-contact probe within a distance in the range from 2-10 μm of the chip, means for monitoring the selectively detected enhanced THz radiation, and means for determining the spectroscopic signature of the material. In addition, the analyte material can be molecules in dilute solutions, wherein the molecules are selected from the group comprising monolayers of biological material and cancer cells.

In addition, the all-optical, apertureless continuous-wave frequency-domain spectroscopic sensor instrument can further comprise means for generating a spectroscopic signature of the test material, means for generating a database of spectroscopic signatures of materials, and means for identifying the analyte material by comparing the spectroscopic signature of the analyte material with spectroscopic signatures of materials in the database.

BRIEF DESCRIPTION OF THE DRAWINGS

FIG. 17 is a graph comparing two simulated spectra for 60 bp sequence of CFT073 *E. coli* strain model presented in Tables 1 and 2.

Figure 18:
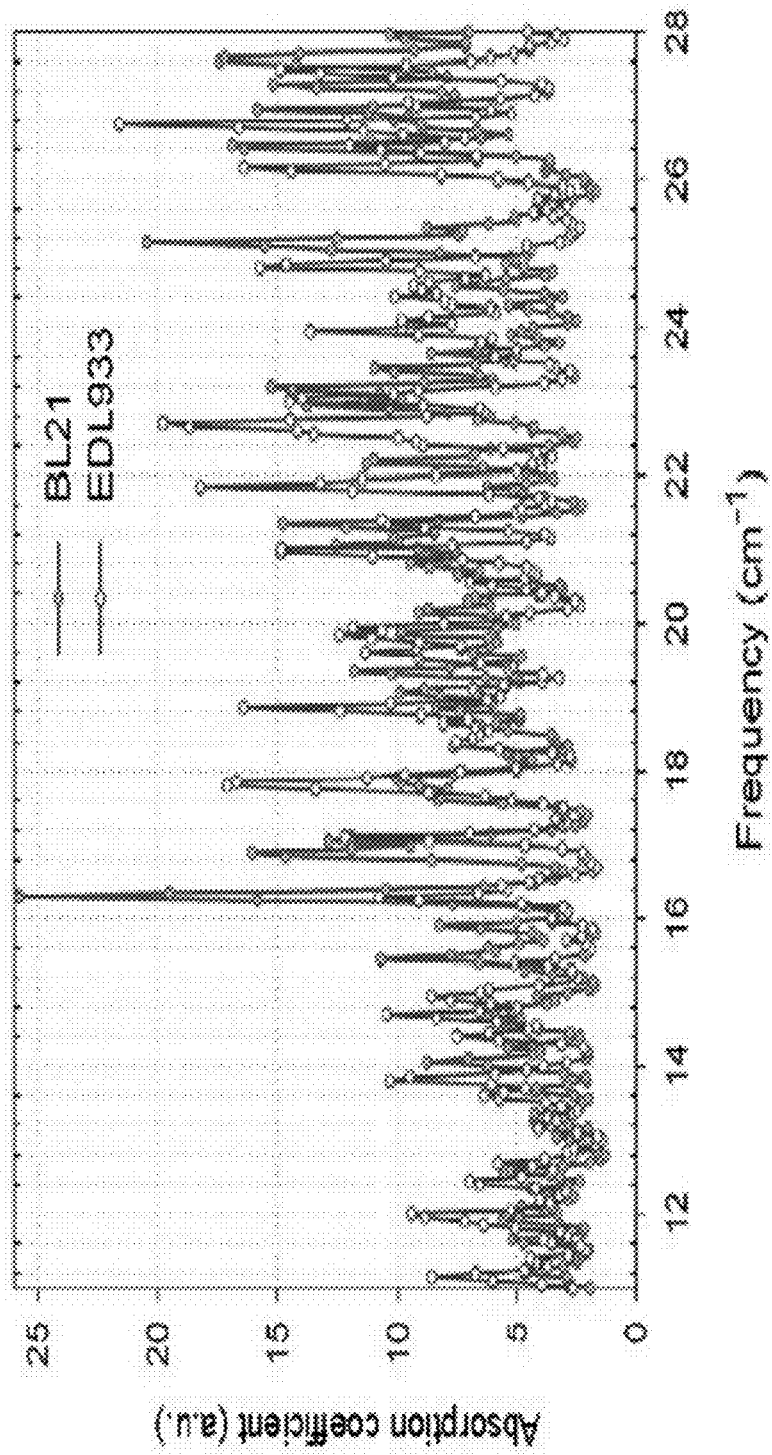

To demonstrate the effect of DNA sequence on their THz vibrational absorption spectra for CFT073 and BL21 was simulated is shown in FIG. 18.

Figure 19:
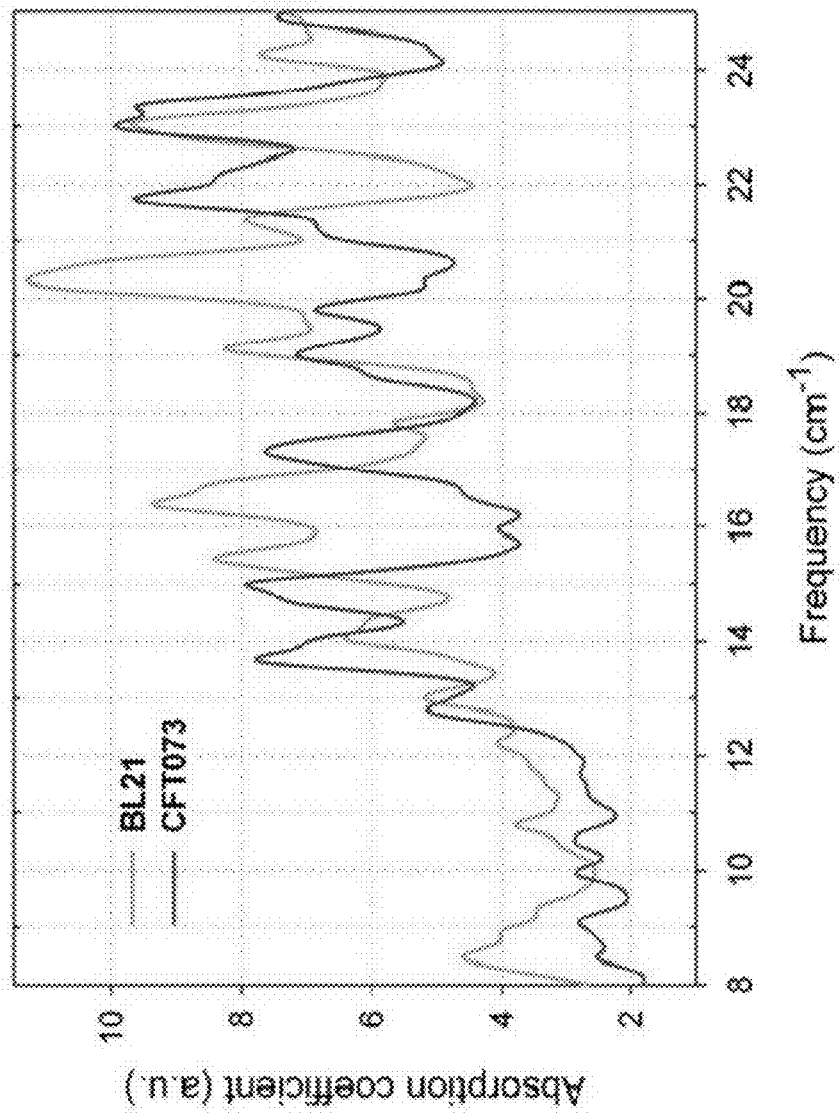

Absorption spectra from non-pathogenic BL21strain and deadly strain EDL933 using 60 bp models (water box 12 A, averaged in all three directions, dissipation factor 0.12 cm-1) are shown in FIG. 19.

Figure 20:
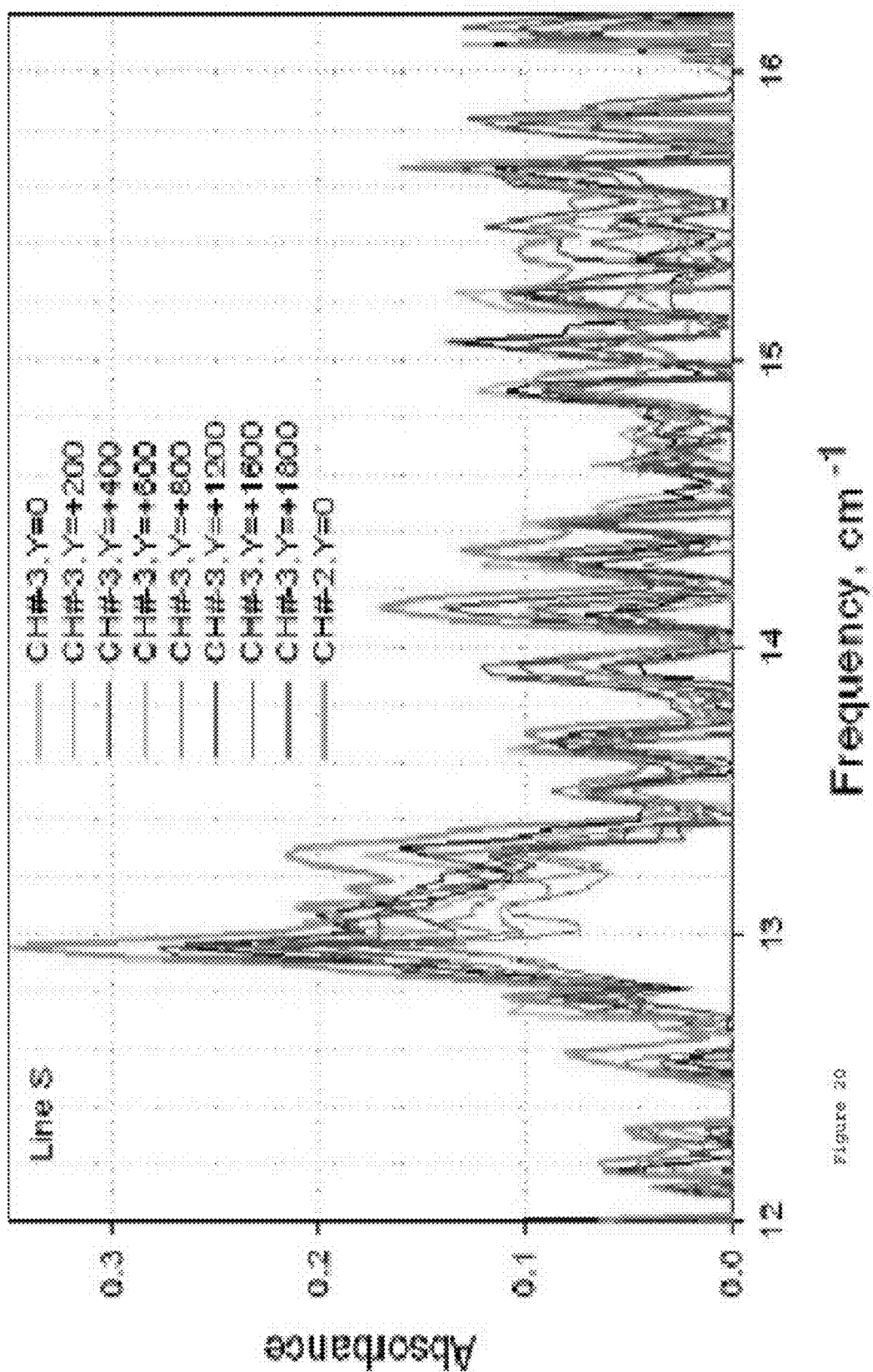
Figure 21:
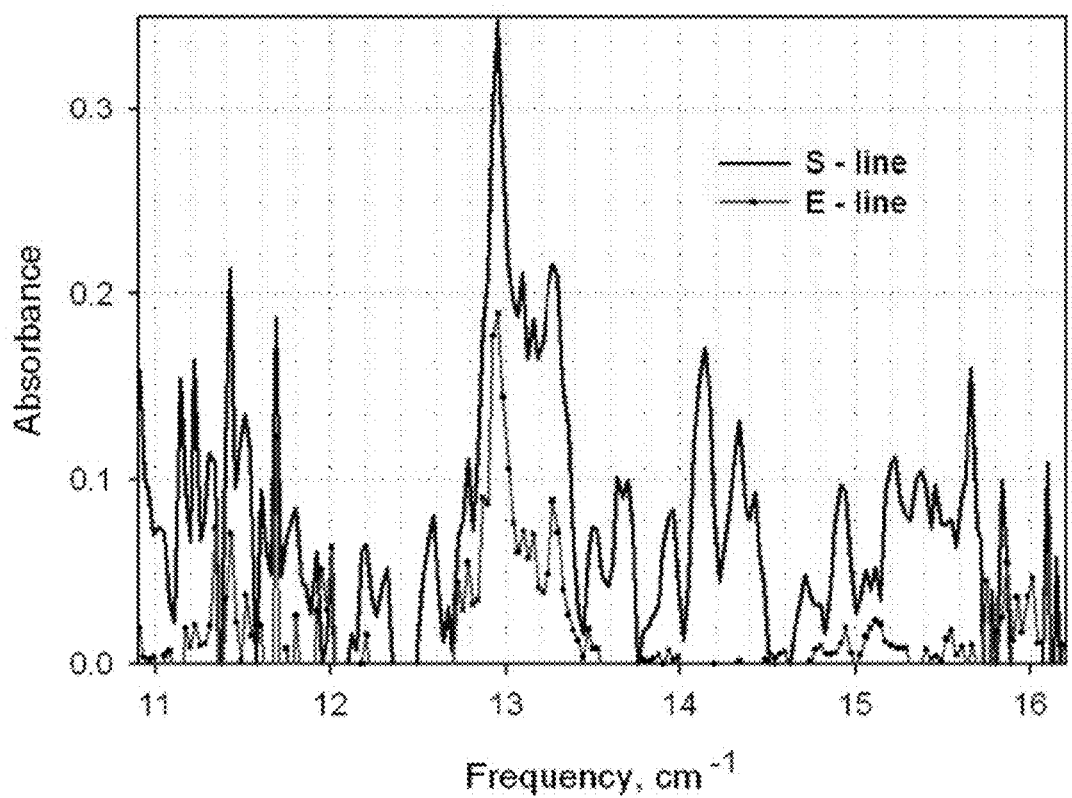
Figure 22:
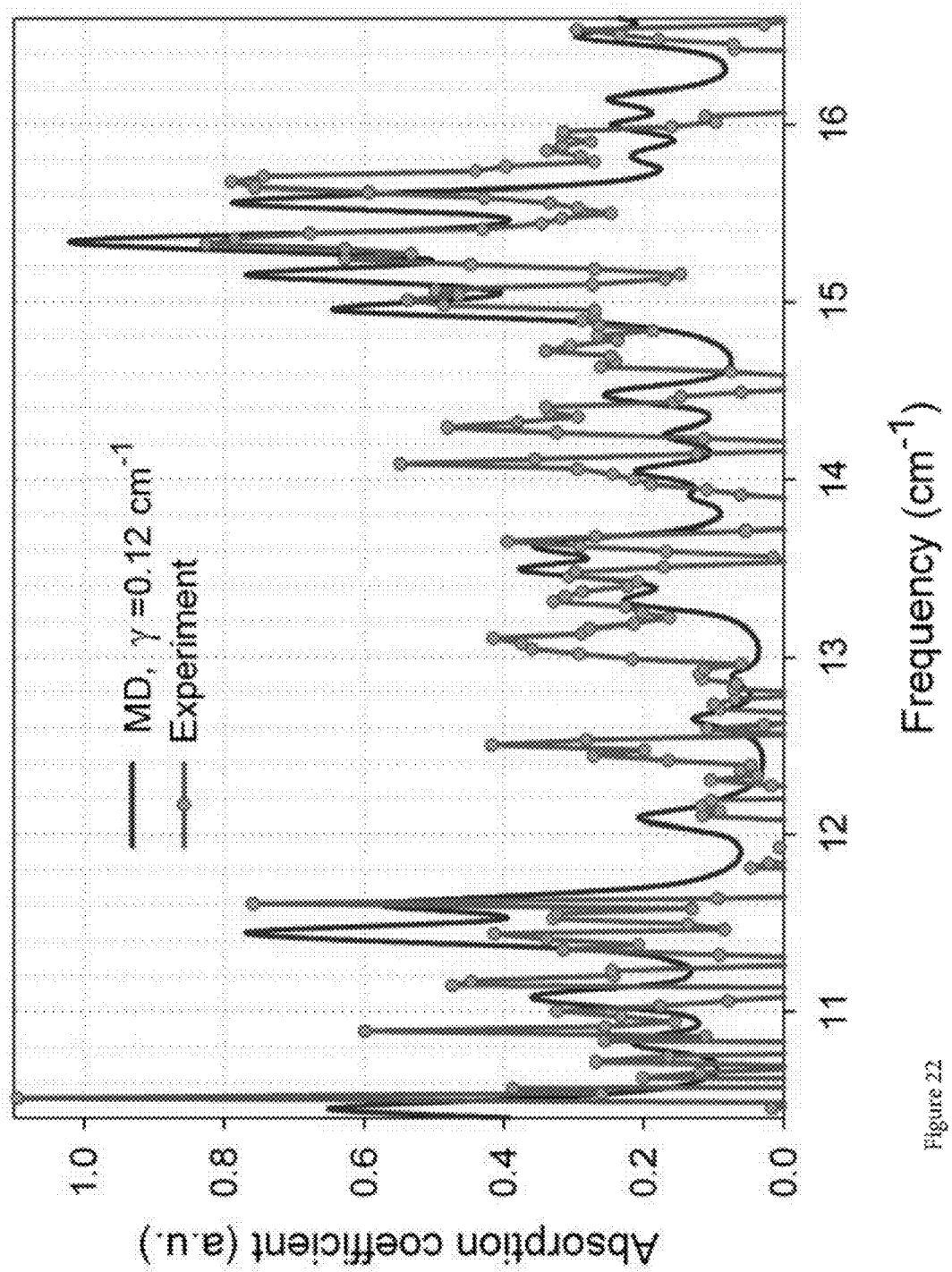
Figure 23:
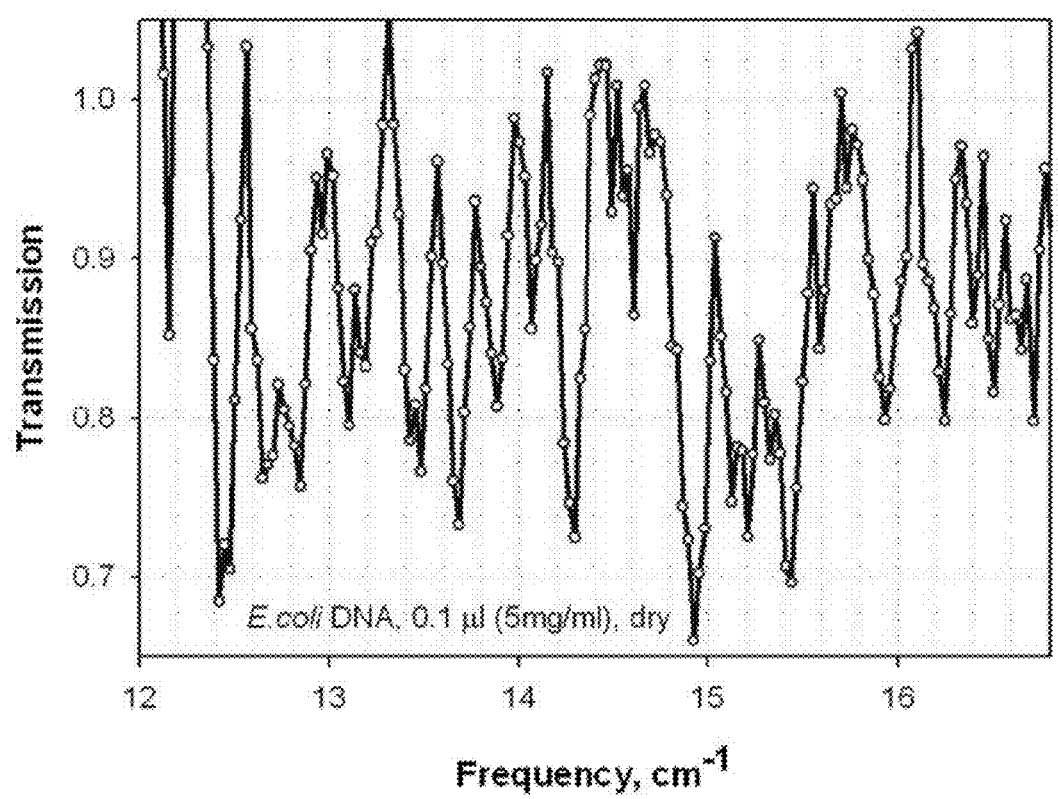
Figure 24:
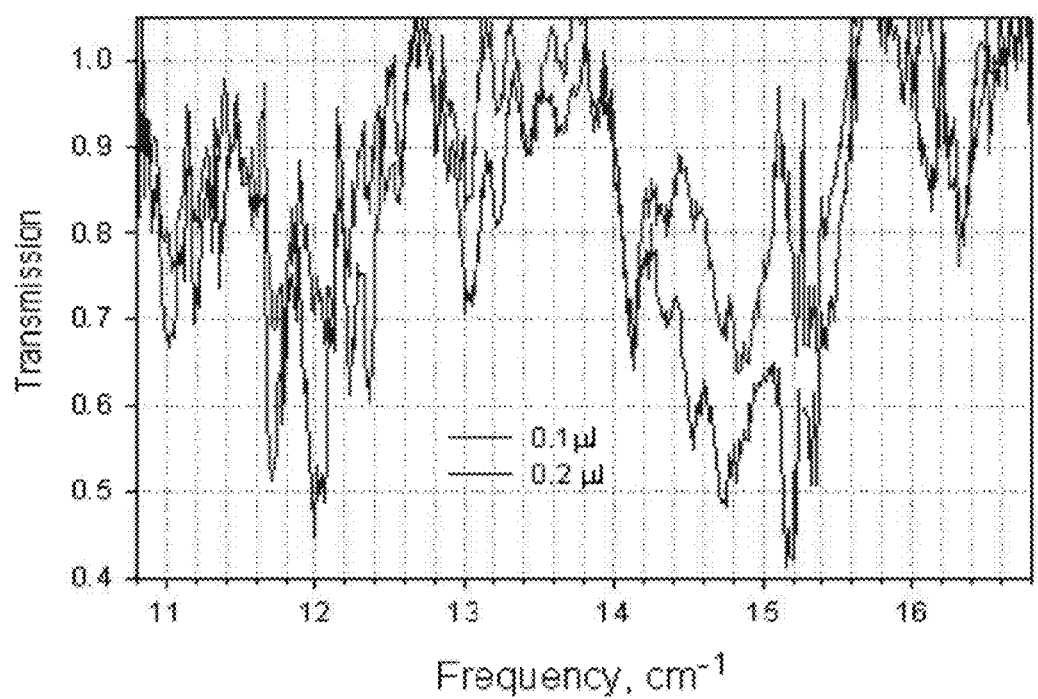
Figure 25:
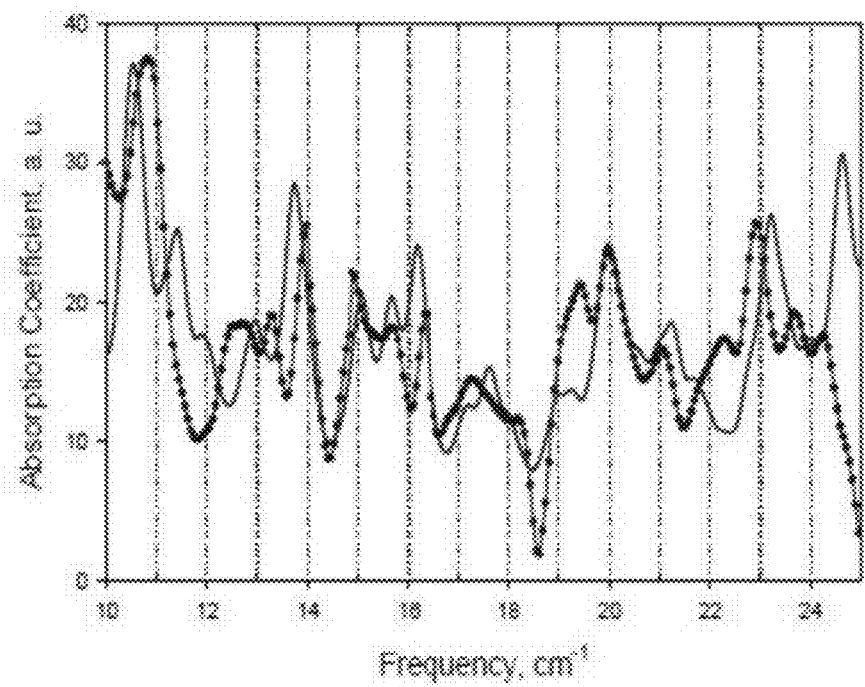
Figure 26:
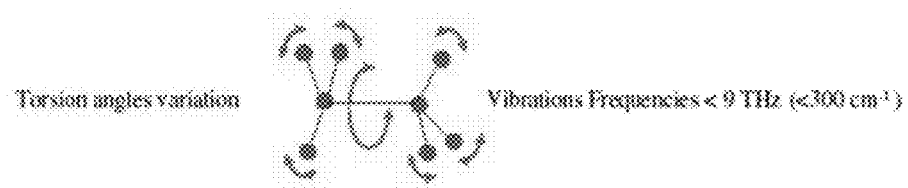

FIG. 20 is a graph illustrating Reproducibility of spectroscopic signature from ovarian cancer cell at different coordinates of a chip FIG. 21 is a graph illustrating the difference in signatures from two lines of ovarian cancer cells FIG. 22. Absorption spectrum of protein thioredoxin from *E. coli*: MD simulation and experimental results as measured using the spectroscopic sensor of the present invention FIG. 23 is a graph showing the transmission spectrum of *E. coli* DNA FIG. 24 is a graph showing the transmission of *E. coli* cells: two samples with different amount of material FIG. 25 is a graph showing THz signature of *E. coli* transfer RNA: experiment-dotted, and model simulation—solid blue FIG. 26 is a drawing of vibrations in the THz frequency range.

DETAILED DESCRIPTION OF THE INVENTION

Figure 1:
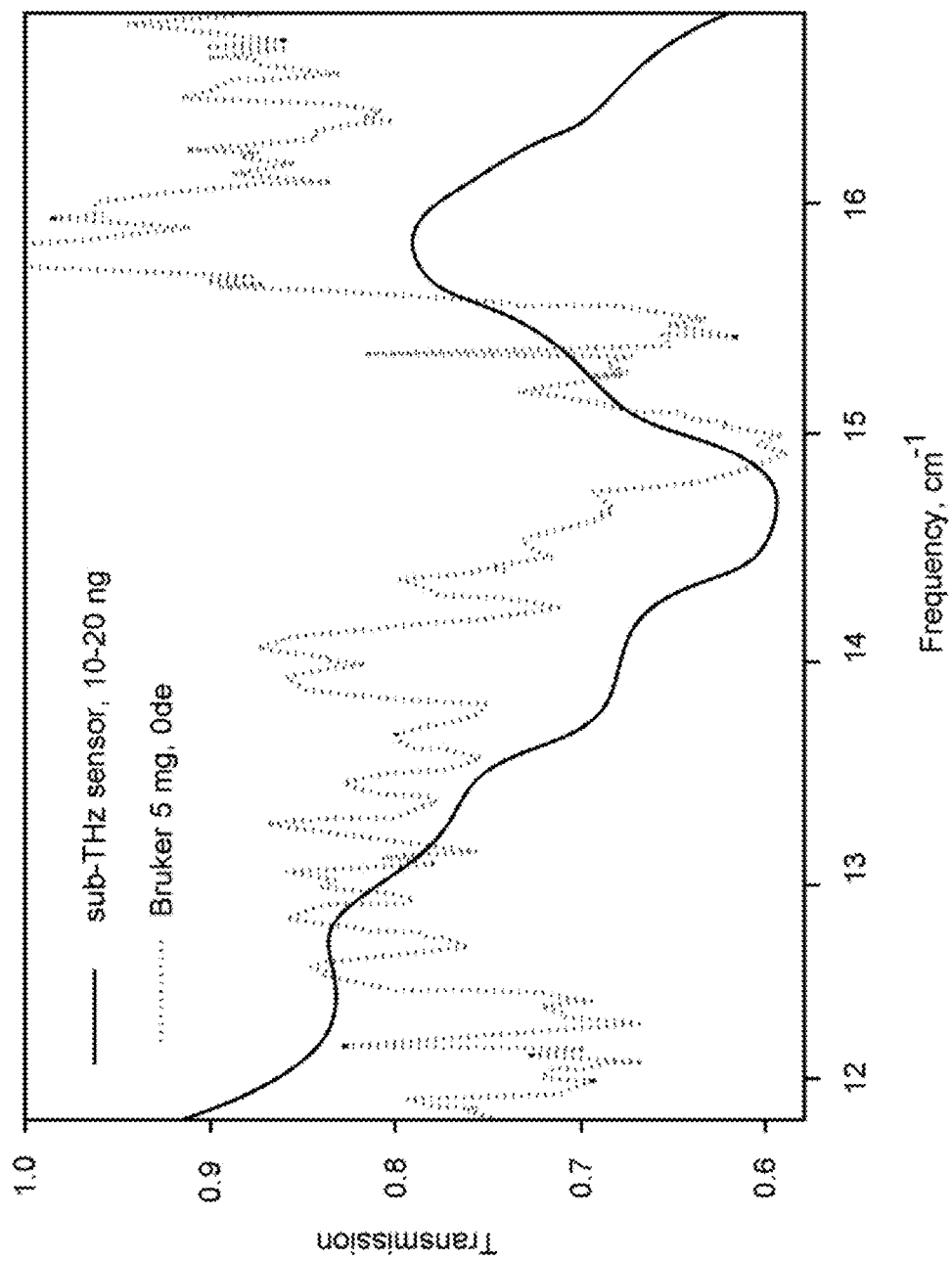
FIG. 1 is a graph of the transmission spectra of *E. coli* measured with a prior art spectrometer and the disclosed spectroscopic sensor objective in accordance with the present invention.

As disclosed in U.S. Pat. No. 8,309,930, which is incorporated herein as though recited in full, the spectroscopic instrument permits observation of vibrational resonances in transmission/absorption spectra of nano-gram quantities of solid biological materials. The system operates in the frequency range between 315 and 480 GHz with a signal noise ratio ~$10^3$ depending on frequency. Transmission spectra from biosimulants, *B. subtilis* (BG), *E-coli* cells, and some molecular components (DNA, thioredoxin) were measured and absorption spectra were calculated. The transmission results for the same biological materials, *E. coli* bacterial cells, obtained with two instruments, are compared in FIG. 1. The different transmission scale for each of the two instruments, as well as the dramatically decreased amount of material required for examination, in the system of the present invention, at least two orders of magnitude difference. The spectra measured with the herein disclosed spectroscopic sensor reveal larger numbers of narrower spectral features with much higher feature intensities. The substrate material and the orientation of biological cells relative to the electric field of radiation are different in these two cases, and shifts in exact position of transmission minima on the frequency scale can be expected because of different orientation of cells.

The waveguide and micro-detector circuit were designed using HFSS simulation to separate THz radiation from a dc Schottky diode signal. Using the instrument, testing demonstrated better than 200 μm spatial resolution, currently restricted by the opening size of the micro-detector waveguide (150×200 μm$^2$). A spectral resolution better than 1 GHz was achieved, along with high sensitivity, a signal/noise ratio of ~$10^3$ (depending on frequency) and at room temperature operation without the requirement for air evacuation, or purging with dry nitrogen.

Figure 14:
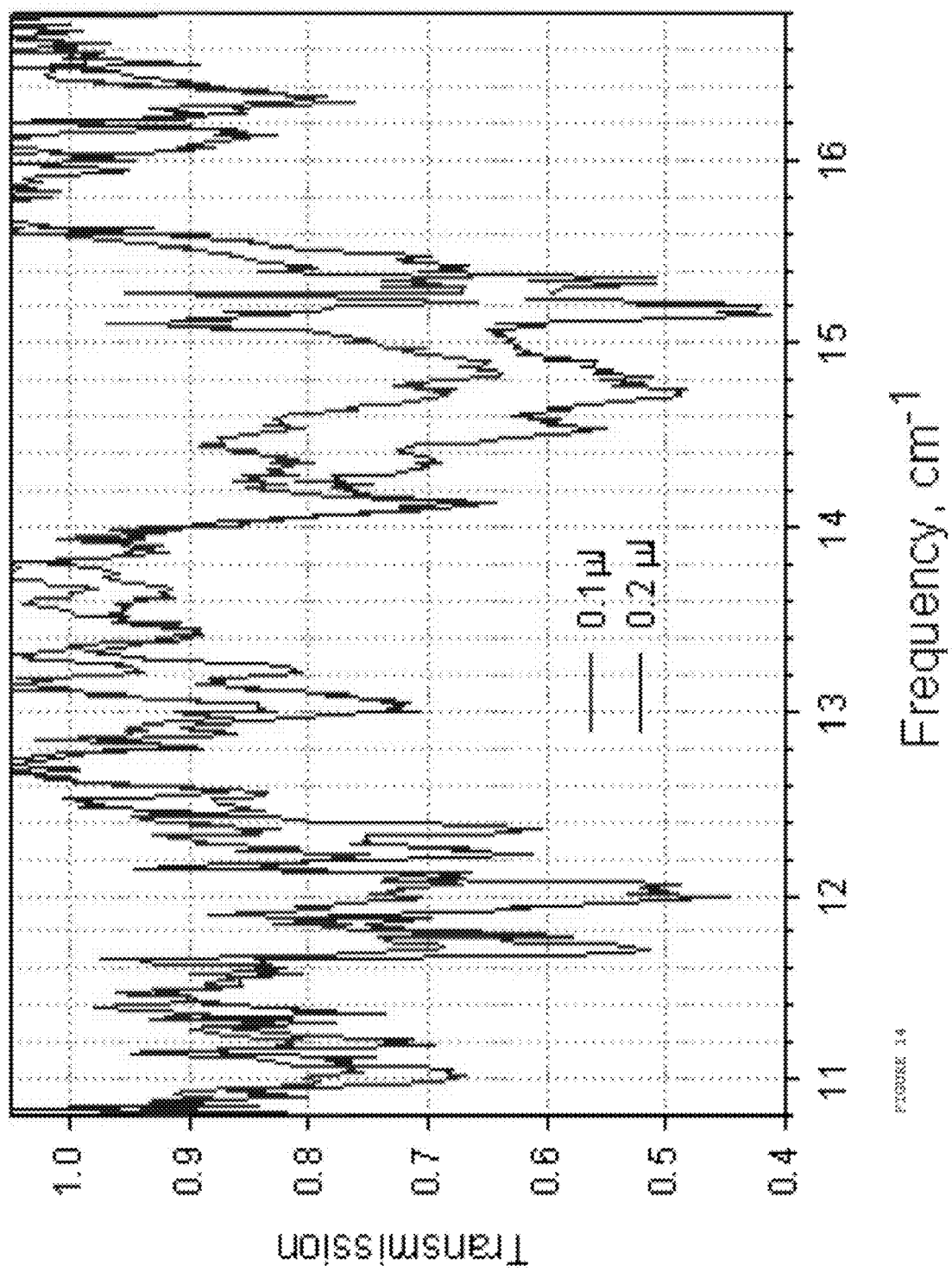
FIG. 14 is titled "Due to high sensitivity, good spectral resolution, and spatial resolution below the diffraction limit, this spectroscopic instrument permits user to observe intense (at least an order of magnitude higher) and narrow spectral resonances in transmission/absorption spectra of nano-samples from biological materials".

For sample preparation, a 0.1-0.3 μl drop of solutions/suspension of biomaterial is micropipette in one spot of the array of micro-channels in the sample holder. Measurements are taken at 10 min following droplet placement, after the sample is dried. The probe for the detection system is positioned several microns above the array. Only ~20 ng of biomaterial is required for the sample in this system as compared to the mg sample size required in the previous work done on the Bruker spectrometer. The new process for coupling allows for dramatic improvements in sensitivity, reliability, and selectivity of terahertz detection systems. Due to high sensitivity, good spectral resolution, and spatial resolution below the diffraction limit, this spectroscopic instrument permits user to observe intense (at least an order of magnitude higher) and narrow spectral resonances in transmission/absorption spectra of nano-samples from biological materials (FIG. 14). In the test experiments it was demonstrated that cellular components contribute to spectroscopic signature of the entire microorganism. As a result, THz vibrational spectroscopy adds quantitative genetic information to the characteristic signatures of biological objects, thus increasing the detection accuracy and selectivity. To demonstrate the capabilities of a new spectroscopy technique, transmission spectra from bacterial cells and some of their molecular components (DNA, thioredoxin) were measured. From the transmission spectrum of *E coli* DNA shown in FIG. 15, the width of spectral lines can be estimated as ~0.1 cm$^{-1}$.

The micro-channels can be about 5-50 μm wide, 1 μm deep, 1-2 μm long, and are in a 10-50 μm substrate of polydimethylsiloxane (PDMS) or polymethylmethacrylate (PMMA), or other material, that is transparent to THz radiation.

Figure 2:
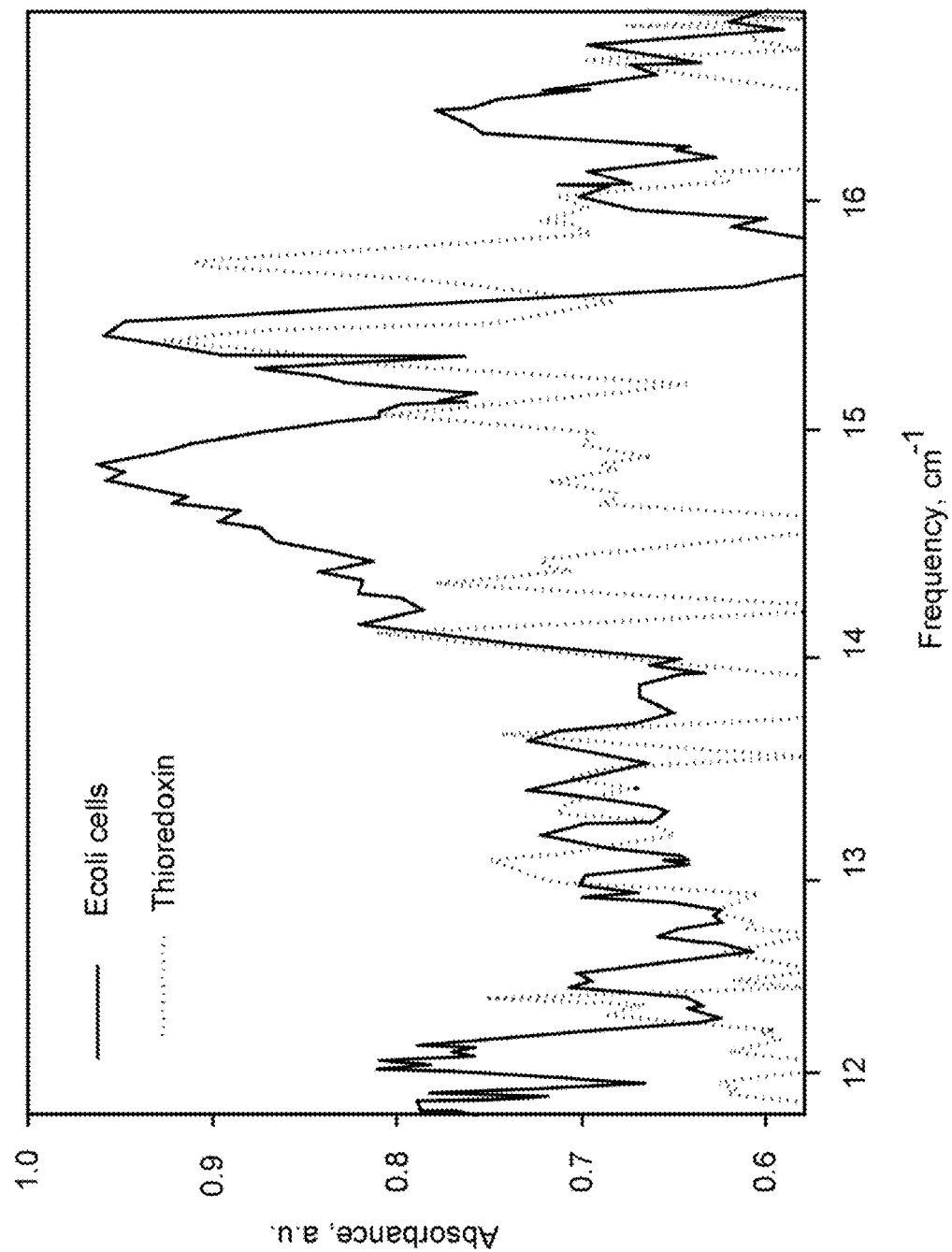
FIG. 2 is a graph of the absorbance spectra of *E coli* cells and one of its protein thioredoxin objective in accordance with the present invention.

Absorbance spectra of *E. coli* and one of its molecular components, the protein thioredoxin, as shown in FIG. 2, demonstrate that the components contribute to the vibrational spectrum of the entire bacterial cell (for example, features at 15.35 cm$^{-1}$).

Figure 8:
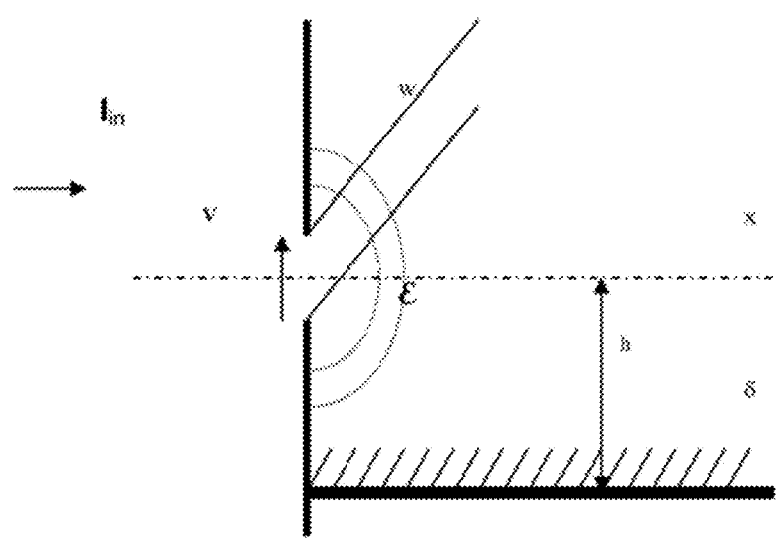
FIG. 8 illustrates an example arrangement of a waveguide in accordance with the present invention.

To further confirm the reality of the observed narrow and intense resonance features in the sub-THz transmission/absorption spectra of biological materials as measured with the new spectroscopic sensor, the measured spectrum from the *E. coli* protein thioredoxin is compared in FIG. 8 with computational modeling results using MD simulations with a damping factor of $\gamma=0.12$ cm$^{-1}$ that is adequate to the width of spectral lines. The overall correlation between the theory and experimental data confirms again the existence of intense and narrow absorption lines, which can be used for discrimination between different materials.

Figure 3:
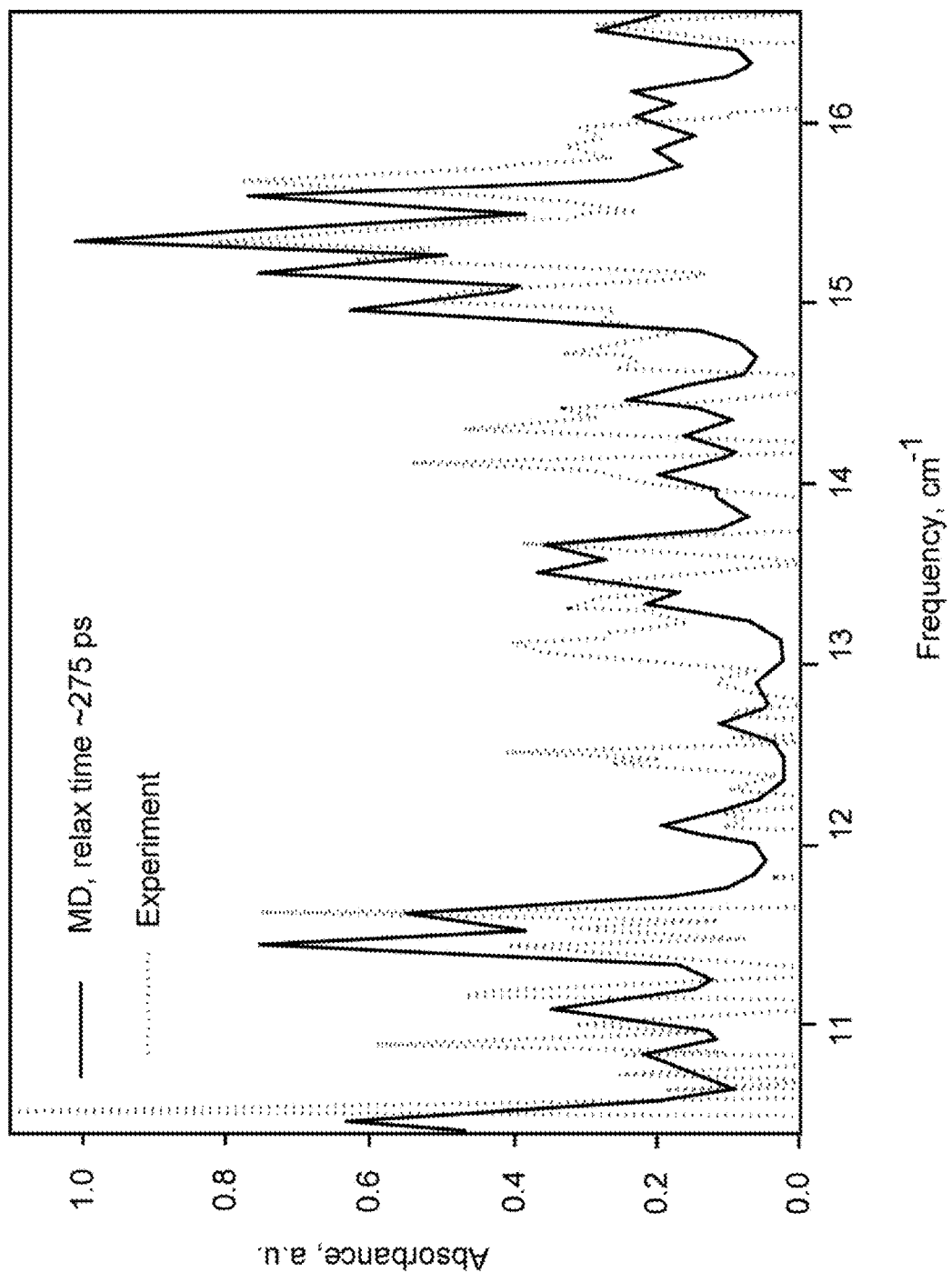
FIG. 3 is a graph of the absorption spectrum of the protein thioredoxin from *E. coli* objective in accordance with the present invention.

Absorption spectrum for thioredoxin from *E. coli* is compared with MD simulation in FIG. 3. Not all peaks are reproduced in the measured and simulated spectra since simulation parameters, however, the overall correlation between the theory and experiment confirms again the existence of intense and narrow absorption lines, which can be used for discrimination between different bacteria and strains.

The computational modeling procedure was conducted exactly as it was described in detail in N. Alijabbari, V. Chen, I. Sizov, T. Globus, and B. Gelmont, "Molecular dynamics modeling of the sub-THz vibrational absorption of thioredoxin from *E. coli*," J. Mol. Model, vol. 18, no. 5, pp. 2209-2218, May 2012. The only difference was the smaller value of the dissipation factor in the current work (0.12 cm-1) that is close to the approximate experimental widths of spectral features observed with the new instrument. Again, due to possible contributions from several different modes occurring at close frequencies, the width of spectral lines gives us an upper limit of $\gamma$. As seen in FIG. 3, not all peaks are reproduced in the measured and simulated spectra, since simulation parameters have not yet been optimized. Besides, the same value of $\gamma$ was used to calculate absorption for all vibrational modes, and that is not necessary the case. However, the overall correlation between the theory and experimental data confirms again the existence of intense and narrow absorption lines, which can be used for discrimination between different bacteria and strains. The existence of such long-lived vibrations was confirmed in recent experimental results on relaxation time scales in thioredoxin from femtosecond-resolved fluorescence spectroscopy. In addition to the dynamical processes on the time scale of 95-114 ps, it was observed that longer quenching dynamic processes with time scales of 275-615 ps at a hydrogen bond distance, which can give local fluctuations with vibrations spectral line widths less than 0.1 cm-1.

Computational prediction and a demonstrated spectroscopic results with high spectral and spatial resolution, which resolves large number of highly intense and narrow absorption lines, gives completely new information about the interaction between THz radiation and biological materials. This creates the basis for high discriminative capability between bacterial strains in extremely small sample volumes. The width of observed spectral lines between 0.05 and 0.1 $cm^{-1}$ corresponds to the scattering time of motions between 670 and 330 ps. The existence of such long living vibrations was also seen in recent experimental results on relaxation time scales in thioredoxin from femtosecond-resolved fluorescence spectroscopy. In addition to dynamic processes in the time scale of 95-114 ps, which is very close to the relaxation time in the above results with the Bruker spectrometer, longer quenching dynamic processes was also observed with time scales of 275-615 ps at a hydrogen bond distance, which can give local fluctuations with vibrations spectral line width of 0.12-0.054 $cm^{-1}$.

The disclosed results from measurements with high spectral resolution demonstrate very intense and narrow spectral features from biological molecules and bacteria with widths between 0.05 and 0.2 cm-1 compared to previous detection using a resolution of 0.25 $cm^{-1}$. The analysis of results also indicates that the coexistence of diverse relaxation dynamic mechanisms relevant to sub-THz frequency region.

It has been observed that multiple intense and specific resonances in transmission/absorption spectra from nanogram samples with spectral line widths as small as 0.1 $cm^{-1}$ provide conditions for reliable discriminative capability, potentially to the level of strains of the same bacteria, and for monitoring interactions between biomaterials and reagents in a near real-time. However this sensor could only be used to characterize samples in a solid state, which was a laborious, imprecise, and time-intensive process: empty channels 150 microns wide on a 1×1" chip had to be scanned and characterized, one by one, to establish background readings before the sample, which might be as small as 2 microns was placed on the chip and all the channels rechecked.

The disclosed method uses a highly sensitive frequency domain resonance spectroscopy with high spectral and spatial resolution for characterizing ultra small amounts of materials that have active absorption modes at frequencies from 4-40 $cm^{-1}$. The spectroscopy system uses a THz source of radiation and a micro-detector with a microcircuit, both suitable for operation somewhere within this range, a motorized, or mechanical, stage for holding a micro/nanofluidic chip for a sample material, and a three-dimensional positioning of the components with an accuracy better than 1 µm. The instrument enables observation of narrower spectral lines (0.07-0.1 cm-1 or 2-3 GHz) from biological macromolecules and bacterial cells/spores and dramatically improves the specificity of spectral signatures from biomaterials and discriminative capability of sub-THz vibrational spectroscopy.

Integrated as part of this system is a micro/nanofluidic chip platform with a manifold for precise positioning of a sample material using electrophoretic or other mechanism of liquid movement, a plasmonic device to effectively couple radiation passed through the sample and deliver this radiation into the detector waveguide, a high resolution optical visualization system to control the positioning, and computer control hardware and software for automatic operation of the system. Sub-THz electronically tunable source based on Schottky frequency multipliers (Virginia Diode, Inc) and a sub-micron precision motorized stage for three dimensional scanning capability of a detector subsystem relative to a multi-channel chip sample holder. The frequency range is between 325 and 490 GHz with an average output power of ~0.2 mW.

The detector system entails a micro-detector (Schottky diode, VDI) with a replaceable beam lead microprobe and a planar microdetector circuit mounted in a custom micro-waveguide housing. The sample holder is constructed as an array of micro-channels in a gold layer on a substrate. This configuration generates the edge effect necessary for enhancement of the EM field of the THz radiation and provides regions for holding bio-material. Any material with a low absorption coefficient and low refractive index in the THz range can be used as a substrate, for example a polymethyl methacrylate (PMMA) substrate with channel widths of 5-20 µm. The thickness of the gold layer (2-5 µm) determines the channels depth.

A high magnification optical imaging system with a long-working-distance objective enables accurate positioning of components. Data collection options include signal vs. frequency, time, and the three position coordinates. The waveguide and microdetector circuit were designed using HFSS simulation to separate THz radiation from a dc Schottky diode signal.

The basis for the method disclosed herein is a THz spectrometer having high sensitivity, high spectral resolution, and high spatial resolution. High spectral resolution is provided by a frequency source designed to provide radiation in the frequency range of 4-40 $cm^{-1}$ or 120-1200 GHz with a resolution of at least about 1 GHz. Spatial resolution is provided by the width of the nano/micro channel, in which the sample is contained during the analysis; through this technology, resolution less than the diffraction limit can be achieved. These factors enable the observance of vibrational resonances in transmission/absorption spectra of solid and liquid nano samples from biological materials.

High sensitivity is provided in the system by the use of near field detection, which the probe for detection is brought close to the channel in which the sample is contained. As part of this method for increasing the sensitivity, and resolution of the analytical method, a number of additional improvements are disclosed which contribute to improving the utility of this method for biosensing applications. A sample material cell is a multichannel array sample holder with a periodic structure for local enhancement of the electromagnetic field of the THz radiation with respect to the incident field through the use of the discontinuity edge-effect and the extraordinary transmission of a sub-wavelength-slit.

As disclosed in the aforenoted '930 patent the novel micro/nanofluidic device ("chip") platform with a manifold: The novel nanofluidic sensor device (chip) can be integrated with commercially available or with custom-made THz spectroscopic instruments of the present invention for bio detection at sub-wavelength resolution. The chip technology meets the vital criteria of being robust and reliable, easy and simple to use, yielding rapid results, low in cost, and disposable.

To achieve the optimum results, the material for the chip must have low absorption of THz radiation, as well as the minimal possible thickness to reduce radiation intensity and sensitivity losses. Preferably the chip has a diameter of one inch or less with a depth sufficient to receive the channels. The channel(s) within the chip are shallow to minimize the amount of sample material to be characterized (in some cases to the level of a monolayer), to reduce the distortion of the electromagnetic field by the sample material, thus reducing the mismatch between the background (empty channel, or the channel filled with solvent for the sample material) signal and the sample signal. The width and depth of the channels are adjusted depending on the material being analyzed. For example, a single strand of DNA would have a channel approximated 2 nm while *E. coli* would have a channel 2×0.5 microns.

No special sample preparation procedure is required. A 0.1-0.3 ml drop of solutions/suspension of biomaterial is micro-pipetted in a spot of the array of micro-channels in the sample holder.

The chip also has a cover seal that must also be as thin as possible for the near field sensing. This permits the probe, which accepts the radiation passed through the channel (slot) in the chip and carrying the signal information from the background or the sample material, to be as close to the channel as possible. The cover seal is also required to enable the sample to flow through the channel(s) under precise control by either pressure or electrokinetic based methods. The cover seal also protects the sample from evaporation, because the chip channel(s) are extremely narrow and shallow. The sample is further protected by the cover seal from contamination. Thus, the cover enables direct analysis of liquid material samples, which is a marked improvement over previous methods of allowing the liquid to dry and then scanning the residue.

The structure and function of the chip: The chip is comprised of multiple layers of thin plastic, or equivalent, films that are fused together. The material used for the chip fabrication and the method of manufacturing are dictated by the requirements described above. The inner layer contains channel(s) through which a fluid can flow. The channel width can be in micro or nano ranges. The bio material to be analyzed is introduced to this fluid, which is then transported to the channeled area of the chip for the actual scanning. The primary concern with the material of manufacture is that it absorbs no, or little, THz radiation. The phrase "low THz radiation absorption" means that the level of absorption is below the threshold where absorption has a negative influence on the accuracy, reproducibility, or reliability of test data, as would be readily determined by one of ordinary skill in the art who has been instructed in regard to low THz absorption being a required property.

Figure 5:
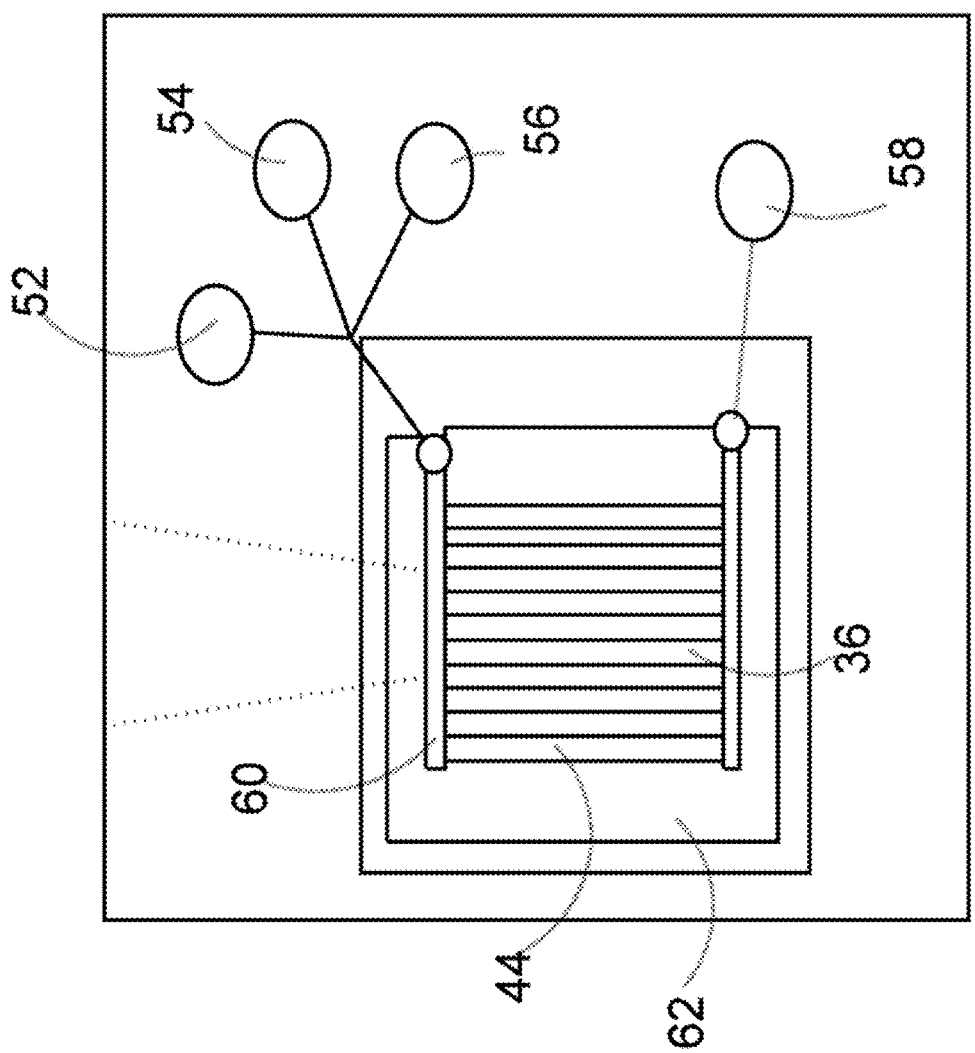
FIG. 5 is an example schematic diagram showing chip, multiple inlet reservoirs and channels leading to the main channel in accordance with the present invention.

As an example illustrated in FIG. 5, sample introduction is achieved by precise automated control of the fluid dynamics, as regulated by a manifold. The manifold also serves to clamp one side of the fluidic chip 44 to a rigid metal base. The manifold, in one configuration, accepts four tubes, three inlet ports 52, 54, 56 and one outlet port 58. Two small screws thread into the metal base, sandwiching the thin fluidic chip 44 between the manifold and the base 62. The area around each of the four fluid ports 52, 54, 56 and 58 is sealed using a small rubber O-ring (not shown). On the opposite side from the manifold, the fluidic chip is clamped to the metal base using two or more screws through a small Lexan bar 60 the same size as the manifold. When properly assembled and in place, the fluidic chip 44 is rigid enough for the scanning process and less subject to mechanical damage during handling. With multiple inlets, the chip 44 enables sample introduction into the channels 36 but also a variety of processes, including mixing samples with reagents and other substances to determine their effects on biomolecules and species, and in-situ flushing of the channels 36 with a neutral solution to enable re-use without the need to remove the chip 44 from the setup. Thus, the device permits serial interrogation of multiple samples.

Figure 4:
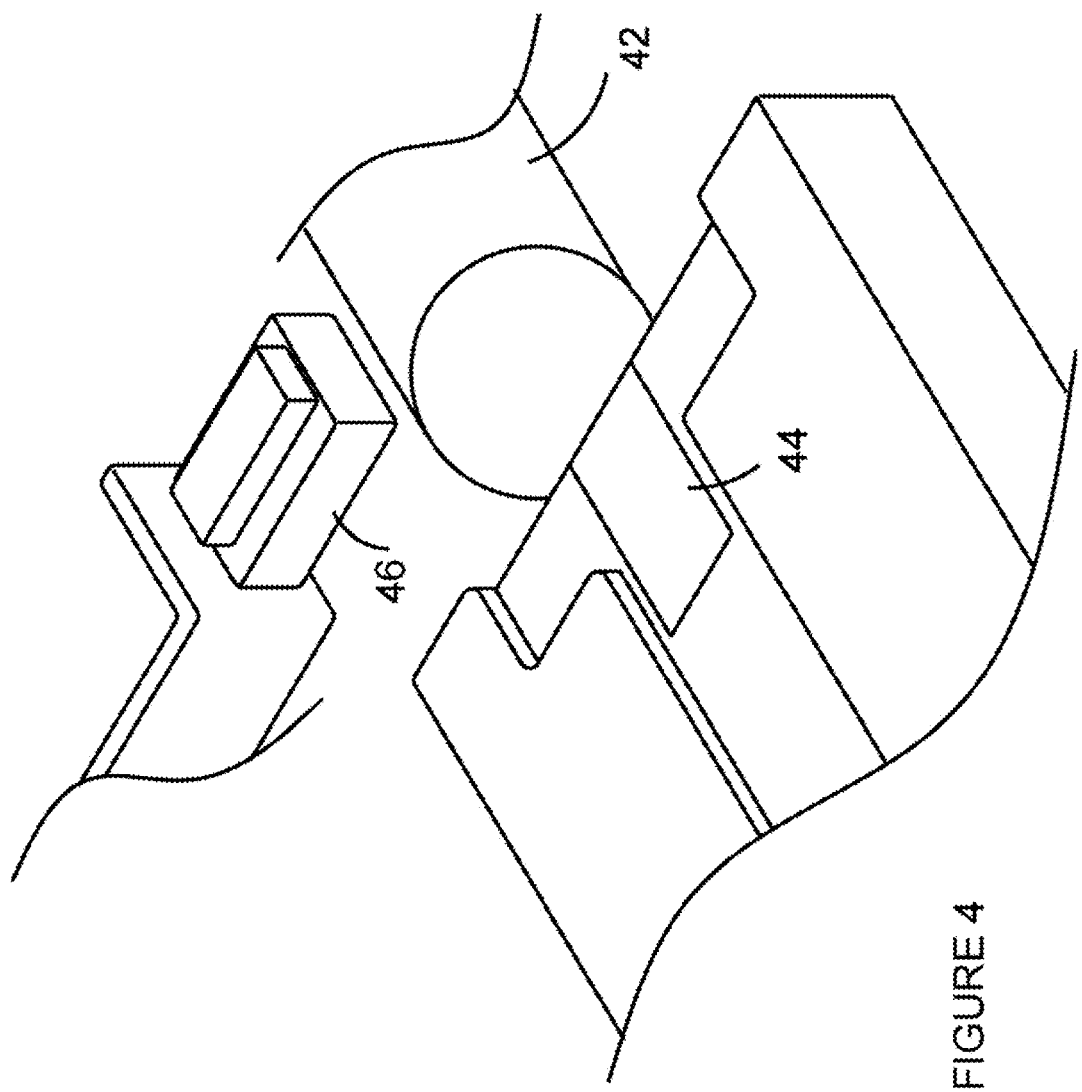
FIG. 4 is an example of the placement of the chip and the objective in accordance with the present invention.
Figure 6:
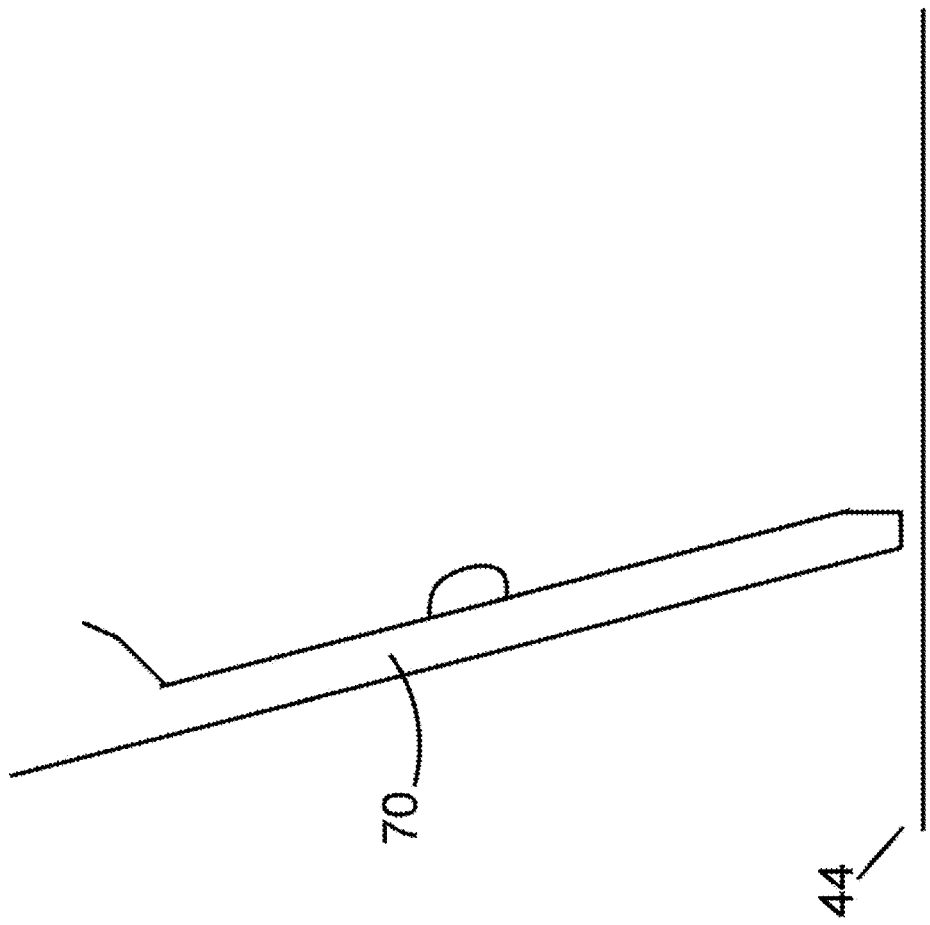
FIG. 6 illustrates the tip and its reflection crossing a channel in accordance with the present invention.

The chip 44 is precisely integrated into the spectroscopy system. Before the scanning starts, the detector with a plasmonic probe on the spectroscopy system shown in FIG. 6 is moved very close to the chip 44 surface. The user must be able to visually observe the position of the non-contact, fragile probe 70 (also referred to as an antenna or wave guide) tip to make certain it is as close as possible to the chip's plastic seal, as required in near field sensing, without actually touching it the seal surface. This is controlled by a microcontroller 46 and software and done automatically with the optical visualization system with the objective 42 shown in FIG. 4 enabling measurement of the distance of the probe 70 from the chip 44. The background scans have to be conducted before the scans with the sample material. The signals from the empty channel or channel filled with a solvent can be used as backgrounds depending on experimental goals. Transmission can be calculated as a ratio of a sample signal to the background. Absorbance of material can be calculated from transmission results. The system permits scanning as functions of frequency, 3-D coordinates of the probe relative to the channel, with the accuracy of ~1 micrometer, or as a function of time for a real time study of biological and biomedical processes.

2. The probe/coupling: Another novel and critical component is the device for coupling the THz radiation passed through the microfluidic channel containing a sample material. The simplest device is a metal probe (it can be gold) with a minimum length of about 50 microns as shown in FIG. 6; the tip (and its reflection) are crossing a channel. This probe works as an antenna or waveguide to deliver the radiation carrying the signal information into the waveguide of the micro-detector. The probe in FIG. 6 can be integrated with a micro-detector circuit inside the housing.

Figure 7:
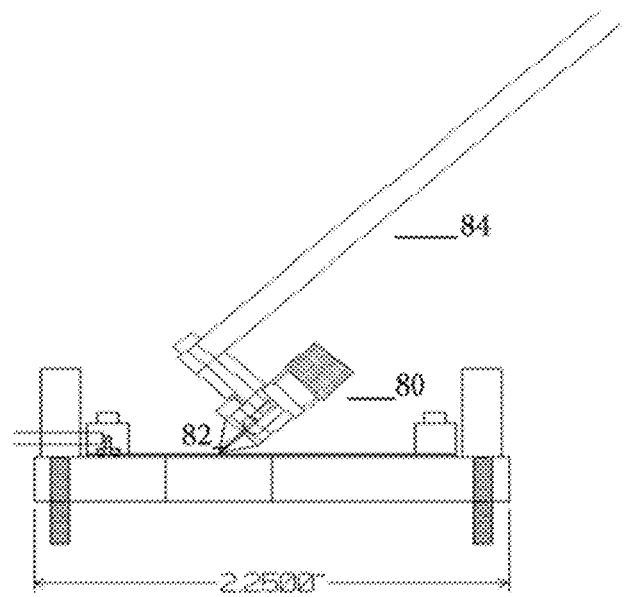
FIG. 7 is a side view of the probe illustrating an example angle of the probe tilt to the direction of THz radiation propagation for the efficient coupling in accordance with the present invention.

The optimal angle of the probe (waveguide or antenna) tilt to the direction of THz radiation propagation for the efficient coupling can be determined using various embodiments, one of which is shown in FIG. 7.

As is shown in FIG. 7, the angling is accomplished by increasing the housing's 80 angle leading to the tip 82 and is adjusted to optimum for the sample using a special arm 84 with precise control of an angle. In the this Figure the arm 84 is holding the modified sloped housing 80 with the standard connector for the measured signal at the top of the housing that does not consist of similar halves, as might be expected; instead, the housing has a large bottom (close to the arm 84) that completely surrounds a much smaller top (near the chip surface). These parts are fastened together with small screws. However, because the "bottom" now surrounds the top on three sides, there is no need for locating pins to register the mating parts; instead, close dimensional tolerances on the three edges accomplish this.

Devices for coupling the THz radiation passed through the nano/microfluidic channel containing a sample material to probe waveguides require excitation of axial surface waves in the plasmonic waveguides. A novel approach was developed and implemented in this method using one important case when axial surface waves are generated in a dielectric-coated metallic guiding surface ($\mu$ is a dielectric thickness by radiation coming through a horizontal channel slot (the width is W) situated above the guiding surface, as illustrated in FIG. 8; however this type of waveguide has no losses to transfer the radiation at the longer distances.

A method to predict the excitation efficiency depending on geometrical parameters shown in FIG. 8. The graphs of FIGS. 9 and 10 demonstrate the dependence of the excitation efficiency on the distance (height h) of the slot above the surface of a waveguide and a thickness of the dielectric, $\mu$m when the width (w) of the slot is equal to 0.5 mm. The efficiency is defined as the ratio of the THz radiation passed through the slot and guided along the waveguide axis x to the flux of incoming radiation $I_{in}$ over the slot width. The example results are shown in the FIGS. 9 and 10 for two frequencies of 300 GHz and 500 GHz.

The enhancement of the THz radiation field and corresponding far-field transmission through the single rectangular aperture (a single slot) is observed with a factor of ~2. The maximum is observed at the dielectric thickness of 0.1 mm for the frequency 300 GHz.

This configuration will transfer THz radiation passed through the sample material in the slot to the detector waveguide opening. Another example for this device uses a dielectric waveguide with electromagnetic field that is different from the dielectric-coated metallic waveguide. The metallic layer can roughly be considered as mirror; thus, the electromagnetic field does not exist below the dielectric-coated metallic waveguide. In dielectric waveguides the electromagnetic field below the waveguide is of the same order as the field above waveguide. The excitation efficiency in this case is lower than for a coated metal; however this type of waveguide has no losses to transfer the radiation at the longer distances.

Figure 11:
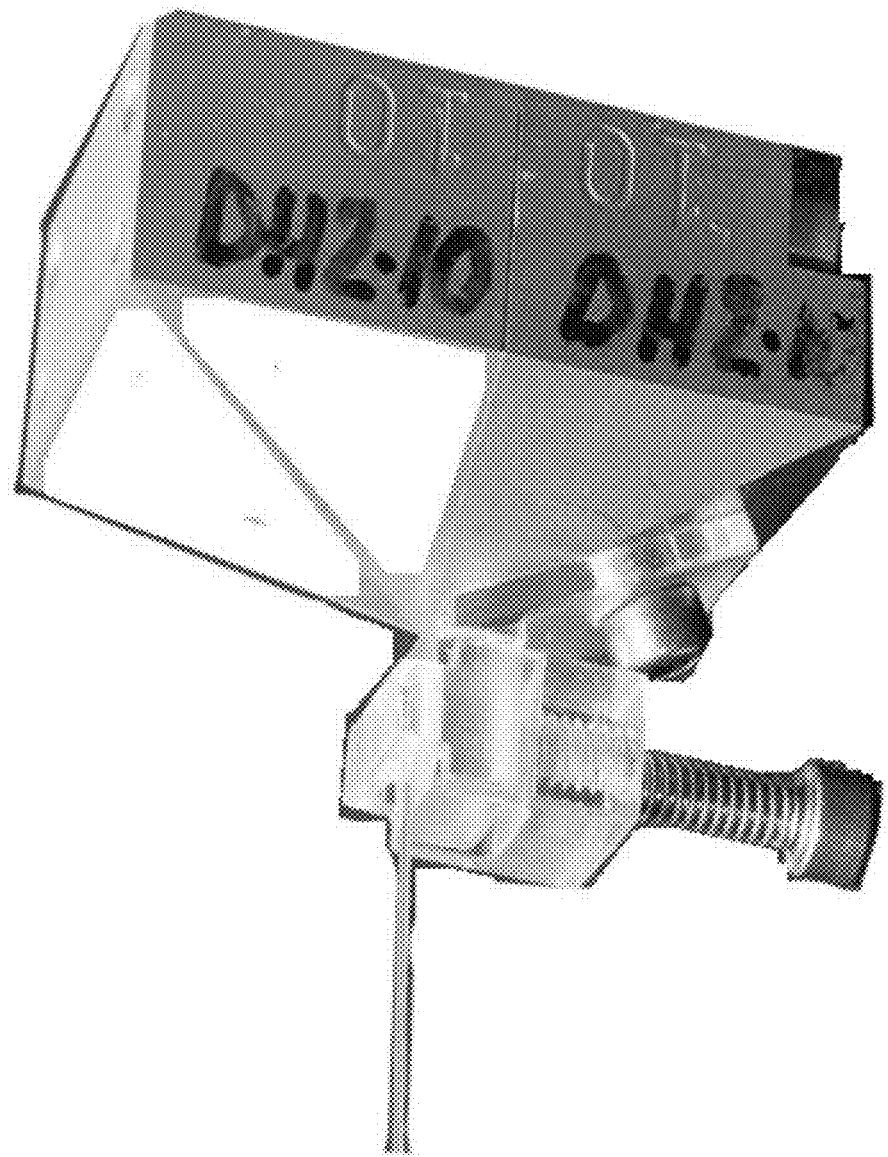
FIG. 11 illustrates the an embodiment using open detector housing to couple the THz signal to the detector chip via a ribbon waveguide, with a micro-detector and a microcircuit of a biosensor in accordance with the present invention.

Another housing embodiment is an open detector housing to couple the THz signal to the detector chip via a ribbon waveguide, as illustrated in FIG. 11, with a micro-detector and a microcircuit of a biosensor. A THz diode chip with the microcircuit is permanently mounted in a small channel. The electrical output signal from this detector chip is routed through a larger intermediate circuit in order to make the transition from bonding wire to wire; this is finally routed to a standard SMA radio-frequency connector at the rear of the housing. A ribbon or a wire waveguide is attached to the front of the housing. In one example configuration, the ribbon measures ~127 μm wide by ~18 μm thick on a 25 μm thick polyimide base, and held in place by two plastic insulators and screws. Because this attachment is purely mechanical, these both housings enable repeated installations and removals of various experimental ribbons, as well as adjustment of any ribbon's position relative to the detector circuit to maximize its coupling of the THz signal to the detector chip.

Computational Modeling

Computational modeling technique to simulate and predict low frequency spectroscopic signatures of large macromolecules of DNA, RNA, proteins and other molecular components of bacterial cells using the energy minimization, normal mode analysis and molecular dynamics (MD) approaches have also been developed. Multiple resonances due to low frequency vibrational modes within biological macromolecules have been unambiguously demonstrated in agreement with the theoretical prediction.

Experimental characterization using the spectroscopic sensor of the present invention, supported by modeling results confirm that highly resolved sub-THz vibrational spectroscopy can be used for reliable and accurate detection of nanograms of *E. coli* using optical, highly sensitive biosensors operating at room temperature with significantly improved ability to discriminate between species up to the level of the strains of the same bacteria.

MD simulations of sub-THz molecular vibrations and absorption spectra of proteins and DNAs targeted two goals: 1) to establish theoretical basis for exploring THz region of electro-magnetic (EM) spectrum for the discovery of new spectral signatures from biological materials; and 2) to improve predictive capabilities of MD computational modeling of THz vibrational absorption spectra from biological molecules. The protein thioredoxin from *E. coli* with known structure is used as a model molecule [pdb ID: 2TRX] to simulate sub-THz vibrational absorption using the software packages Amber 8 and Amber 10 (AMBER Software, CCB Graduate Program; MC 2280, University of California, San Francisco, Calif. 94158-2517 with the procedure modified to improve the convergence of modeling results for proteins.

This small protein contains 108 amino acids, for a total of 1654 atoms. To solvate a sample, an additional 10,500 water atoms are added. Some absorption features predicted by earlier MD simulations agreed reasonably well with experimental data. However, the calculated spectra were highly sensitive to the parameter values, and reproducibility was poor. Amber was empirically parameterized to correctly represent the structural behavior of nucleic acid and protein as would be needed for predicting non-bond-breaking conformational changes. It was not specifically created to simulate low frequency vibrational modes and THz absorption.

MD simulations of sub-terahertz (THz) vibrational modes of the protein thioredoxin were conducted with the goals of finding the conditions needed for simulation convergence, improving the correlation between experimental and simulated spectra, and ultimately enhancing the predictive capabilities of computational modeling. The consistency, accuracy and convergence of MD simulations of the sub-THz vibrational modes were studied by comparing simulations with different initial conditions, protocols and parameters to the experimental results.

Better simulation convergence and improved consistency between simulated vibrational frequencies and experimental data were obtained by using a new procedure for averaging mass-weighted covariance matrices of atomic trajectories in MD simulations. In particular, the open source package ptraj was edited to improve a matrix analyzing function. Averaging of only six matrices gives much more consistent results, with absorption peak intensities exceeding those from the individual spectra and with a rather good correlation between simulated vibrational frequencies and experimental data. It was also found that the choice of the production run length considerably influences the obtained absorption spectra. The optimal time for dividing production run into equal subintervals to calculate individual correlation matrices is equal to ~100 ps. This result is in general agreement with relaxation dynamics time scales of the thioredoxin active center, coupled protein-water fluctuations, and the experimental data on the spectral width of vibrational modes.

3.2. Absorption Coefficient Spectra

Figure 12:
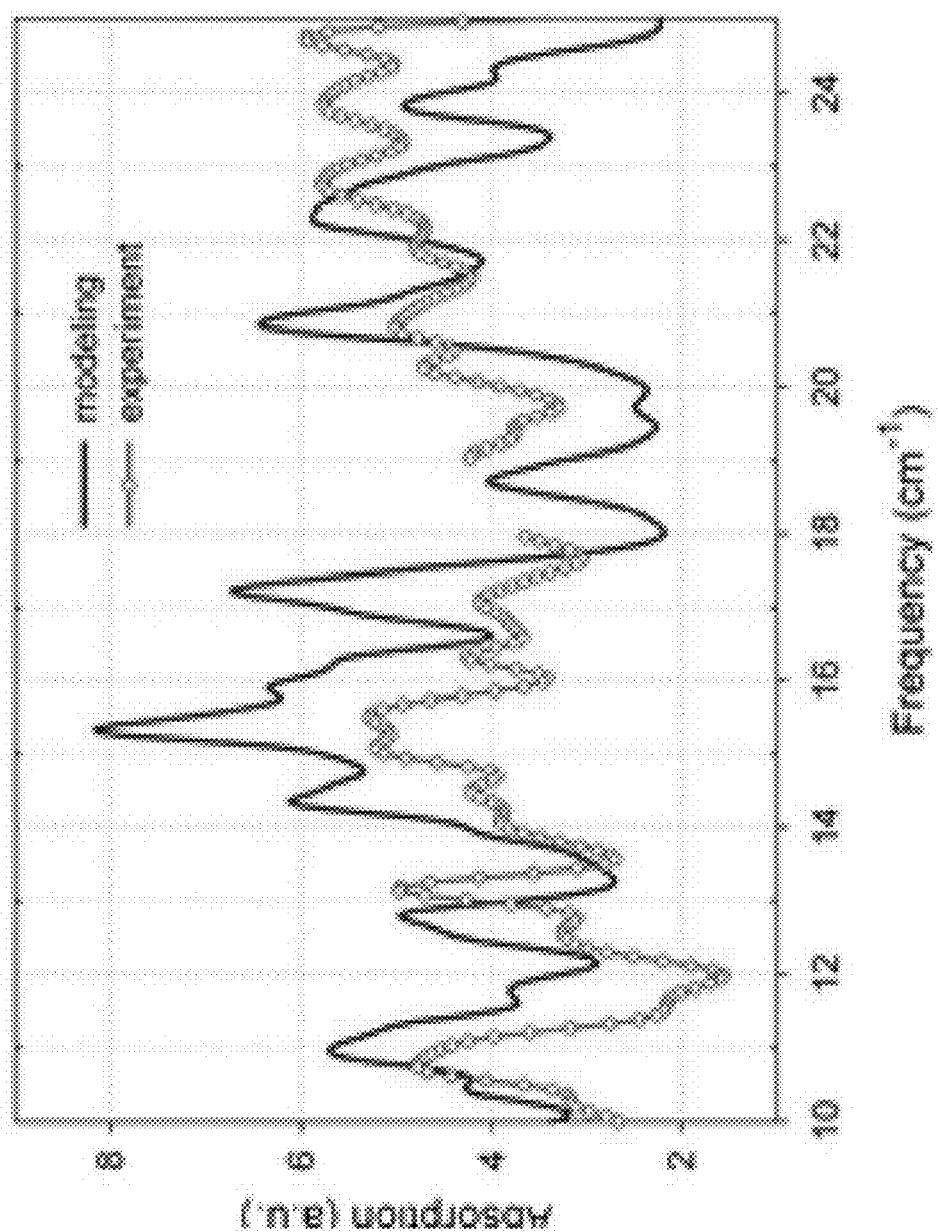
FIG. 12 demonstrates correlation between absorption spectrum of thioredoxin simulated with $\gamma=0.5$ cm$^{-1}$ and experimental results as measured with a moderate spectral resolution of 0.25 cm$^{-1}$.
Figure 13:
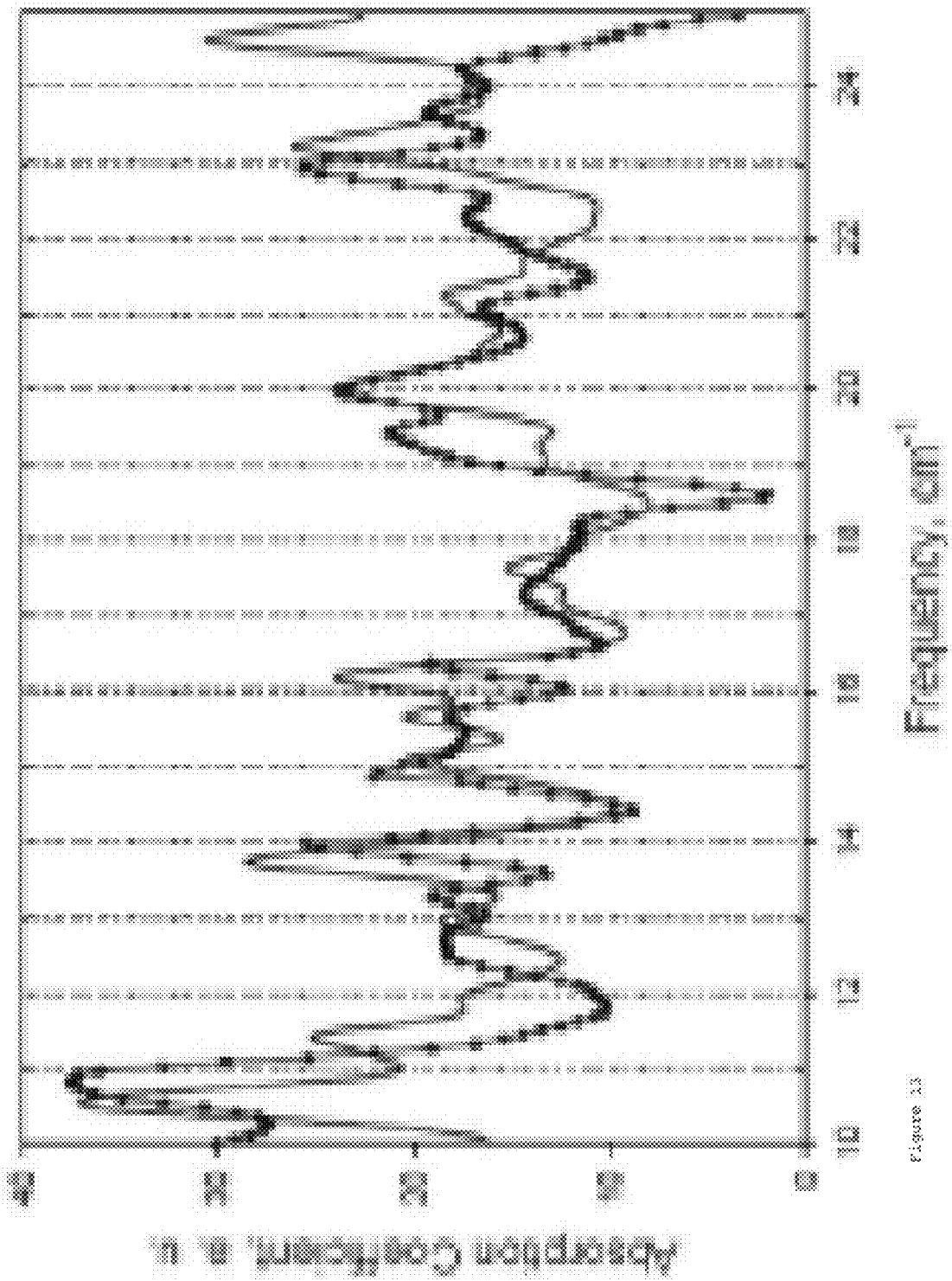
FIG. 13 shows the results of experiment and modeling for a tyrosine tRNA of *E. coli*. Predicted spectral characteristics for bio-simulants were verified.

Atomic trajectories collected in MD simulations are converted to the covariance matrix of atomic displacements ($R_iR_k$) using a quasi-harmonic approximation. The force-field matrix is found utilizing the relation between the covariance matrix and the inverse of the force-constant matrix $((R_iR_k)=k_BT[F-1]_{ik}$ where R—displacements F—force constants. Diagonalization of F matrix gives eigenfrequencies (normal mode frequencies) and eigenvectors (displacement vectors-normal modes). The absorption coefficient spectra $a(v)$ as functions of the frequency $v$ are calculated through the relationship between $\alpha$ and the imaginary part of dielectric permittivity: (1)

$$\alpha(v) = \gamma v^2 \sum_k \frac{S_k}{(v^2 - v_k^2)^2 + \gamma^2 v^2},$$

where $V_k$ are normal mode frequencies calculated by diagonalization of the force-constant matrix, and $S_k$ are oscillator strengths computed for all vibrational modes k. Two values of oscillator dissipation for all vibrational modes in sub-THz range were accepted from experimental works as (moderate spectral resolution in Bruker spectrometer), and γ=0.1 cm$^{-1}$ for a highly resolved spectroscopy using the spectrometer of the present invention. FIG. 12 demonstrates correlation between absorption spectrum of thioredoxin simulated with γ=0.5 cm$^{-1}$ and experimental results as measured with a moderate spectral resolution of 0.25 cm$^{-1}$.

Data Management

A new approach was developed to predict vibrational spectra of complex bio-organisms as fingerprints of bio-simulants and bio-agents that is based on comparison of experimental and simulated vibrational spectra of bio-simulants or components, adjustment of simulated parameters and use simulation to predict vibrational absorption spectra of bio-agents. The experimental database of bio-simulants (*Bacillus subtilis, Escherichia coli*) signatures at THz was constructed, the computational modeling technique was developed and the component based models were created and optimized to simulate the THz spectra of complex bio-organisms as fingerprints of entire bacterial cells or spores, their genetic and other components, DNA, RNA, proteins. Predicted spectral characteristics for bio-simulants were verified. FIG. 13 shows the results of experiment and modeling for a tyrosine tRNA of *E. coli*. Because of bacteria's small size and relatively low absorption coefficient, the THz radiation propagates through an entire object, allowing the genetic material and proteins, all contribute to the THz signature of bacteria or spores. Two most important results were obtained: 1) The THz signatures unique for each bio-agent, and 2) The genetic components (DNA and RNA) contribute significantly into the signature of the entire cell.

Thus, it was demonstrated, both experimentally and theoretically, that THz radiation can be absorbed by optically active internal vibrations of biological molecules. Multiple resonances in absorption (or transmission) spectra of biological materials do exist in the THz and sub-THz frequency ranges. THz transmission (absorption) spectroscopy of biological molecules can reveal these multiple resonances and the spectra can be used for detection and for characterization of bio-polymers including real time monitoring of biological processes, detecting and identification of harmful biological species. At the same time, this technique is non-destructive for living species. In addition, the spectral range below 1 THz is the most attractive for practical applications because of low disturbance from the absorption by water vapors in air and by liquid water or other analytes.

EXAMPLES

Detailed spectroscopic investigations including nucleic acids and proteins were performed over the spectral range from $10\ cm^{-1}$ to $25\ cm^{-1}$ using techniques based upon transmission Fourier-Transform Infrared (FTIR) spectroscopy. Measured spectra of different molecules were analyzed and classified using artificial neural network algorithms. The fundamental physical nature of the observed resonance structure was confirmed by direct comparison of submillimeter-wave spectra measured on short-chained oligonucleotides of known base-pair sequences (12 base pair RNA fragment Poly [C]-Poly[G]) with calculated absorption spectra. Close correlation between calculated and experimentally observed spectra of RNA polymer demonstrated that resonant features result from electromagnetic wave interactions with internal vibration modes in biological macromolecules. Phonon modes should serve as signatures of specific bio-molecules.

Low frequency vibrational spectra for biological materials in solutions were demonstrated. This is important since all functions of biomolecules occur in liquid phase. Applications of THz Spectroscopy for biomedical research were demonstrated via characterization of cancer cells and tissue.

*E coli*

Sub-Terahertz (THz) vibrational spectroscopy is employed to characterize *Escherichia coli* (*E. coli*) bacterial cells and its cellular components. *E. coli* is a diverse bacterial organism that is widely used as a model organism in laboratory studies. However, these bacterial species have strains that can be pathogenic to humans and animals. There are tens of thousands *E. coli* contamination cases every year in United States. Bacteria can adapt to extreme environments and bacterial pathogens share a common trait that is their ability to live long term inside the host's cells.

Traditionally, to identify pathogens from different samples one has to collect and isolate species by using culture methods. The identification process is often relied on microscopic examination to determine phenotypic characteristics of bacterial colony. The final identification of microbial species is assisted by molecular biology and biochemistry methods. Cultivation process alone might last more than one week. Therefore, there is an increasing need for alternative methods that makes the identification of microorganisms fast and reliable. Accurate identification of infectious agents (such as pathogenic bacteria) can be critical for the diagnosis and effective treatment of diseases.

Transmission signatures from sample material in water are well-resolved. As a result, THz spectroscopy provides the advantage of working with samples in the natural environment for biological objects with the minimal sample preparation process.

Molecular dynamic (MD) simulations of proteins and nucleic acids, which make the biggest contribution to THz absorption in bacterial cell, contribute to the understanding of the mechanism of interaction between radiation and biological cells and their constituents, and further improve identification of objects and predict signatures.

Simulated spectra of relatively small biological molecules such as tyrosine transfer RNA or protein thioredoxin from *E. coli* using MD simulations were generated based on comparison between measured and simulated spectra using MD of cellular components. A good correlation of simulated absorption spectra with experimental data was demonstrated. However a large size of macromolecules (~5 million base pairs for *E. coli* DNA) prevents direct application of MD simulation at the current level of computational capabilities. Thus, a simplified short model of the bacterial genome was developed so that the model captures the structure and the most important low-frequency vibrational characteristics of the native DNA. MD simulations of the modeled sequences enable the calculation of expected absorption spectra. Another purpose of statistical modeling of short DNA sequences is to compare their composition and THz spectra obtained for different strains of *E. coli*. The comparison enables the estimation of the uniqueness of THz DNA signatures of individual pathogenic and non-pathogenic strains.

The analysis of the results from MD simulations of the new developed models of DNA sequences from *E. coli* demonstrated that the application of molecular dynamics simulations to the 60 base pair DNA models and to relatively small molecules like a protein thioredoxin from *E. coli* enables the direct study of atomic displacements in molecular dynamics and relaxation processes of intermolecular motions.

Sub-Terahertz (sub-THz) vibrational spectroscopy for biosensing is based on specific resonance features, vibrational modes or group of modes at close frequencies, in absorption (transmission) spectra of large biological molecules and entire bacterial cells/spores. Significant progress in experimental and computational sub-THz vibrational spectroscopy has been made in the last 2-3 years to improve the sensitivity of THz spectroscopic characterization of large biological molecules and microorganisms. Sub-THz spectroscopy was applied to characterize lyophilized and in vitro cultured bacterial cells of non-pathogenic species of E. coli and Bacillus subtilis (BG), spores of BG. Some of cellular components of E. coli, DNA, transfer RNA, and protein thioredoxin were characterized as well.

The spectral range below 1 THz is the most attractive for practical applications because of low disturbance from the absorption by water vapors in air and by liquid water or other analytes. Although liquid water absorbs and contributes to background in the sub-THz/THz spectral range, the level of water absorption in the low THz range is at least 2.5 orders of magnitude less compared to IR and far-IR. Because of low disturbance from water absorption lines, sensors in sub-THz range do not require evacuation or purging with dry nitrogen. Many synthetic materials are transparent in THz region and can be used as substrates or windows for sample cells.

Computational modeling techniques have been developed using the energy minimization, normal mode analysis and MD approaches to understand and predict low frequency vibrational absorption spectra of short artificial DNA and RNA large macromolecules of DNA and proteins. Direct comparison of experimental spectra with theoretical prediction for a short chain α-helix RNA fragment with known structure, transfer RNA and protein thioredoxin from E. coli showed reasonably good correlation thus validating, both, experimental and theoretical results. Vibrational frequencies from simulated spectra for components correlate rather well with the observed features. Thus, multiple resonances due to low frequency vibrational modes within biological macromolecules, components of bacterial organisms, are unambiguously demonstrated experimentally in the sub-THz frequency range in agreement with the theoretical prediction. These results are also in general agreement with analysis of more broad vibrational features observed at higher frequencies using different experimental technologies, mostly on relatively smaller molecules in crystalline form. Organic solid systems and relatively small bio-molecules like protein fragments have been successfully characterized in this range to demonstrate sharp spectral features determined by their individual symmetries and structures.

The ability to discriminate between the different bacterial species quickly and reliably using sub-THz spectroscopy provide significant benefits. In the medical field it can enable a faster and more tailored treatment once a bacterial organism is identified as the cause of an infection The width of individual spectral lines and the intensity of resonance features observed in sub-THz spectroscopy are sensitive to the relaxation processes of atomic dynamics (displacements) within a macromolecule. It is clear that the decay (relaxation) time, $\tau$, is the factor limiting the spectral width and the intensity of vibrational modes, the required spectral resolution, and eventually the discriminative capability of sub-THz spectroscopy. At the same time, the entire mechanism that determines intra-molecular relaxation dynamics is still not completely understood. The suggested range of molecular dynamics relaxation times for processes without biomolecular conformational change varies from approximately 1.5 ps to 650 ps in different studies. The corresponding values for the dissipation factor $\gamma$, and the width of spectral lines, which are reciprocal to $\tau$, are between 0.05 and 20 $cm^{-1}$. Values of $\gamma$ above 1 $cm^{-1}$ would result in structureless sub-THz spectra, since vibrational resonances could not be resolved in this case because of the large density of low intensity vibrational modes. The existence of long-lasting dynamic processes responsible for narrow spectral lines has been confirmed by relaxation dynamics of side chains in macro-molecules observed by time-resolved fluorescence experiments.

Sub-terahertz (sub-THz) vibrational spectroscopy for biosensing is based on specific resonance features, vibrational modes or group of modes at close frequencies, in the absorption (transmission) spectra of large biological molecules and entire bacterial cells/spores. Further improvements in sensitivity, especially in the discriminative capability of sub-THz vibrational spectroscopy for detection, characterization, and identification of bacterial organisms, require spectral resolution adequate to the width of spectral features. Evidences exist for long lasting relaxation processes for atomic dynamics (displacements) resulting in narrow spectral lines and justifying the development and application of highly resolved vibrational spectroscopy.

To increase the sensitivity, reliability, spectral and spatial resolution of sub-THz vibrational spectroscopy techniques, a spectroscopic sensor was employed having imaging capability operating at room temperature, without the need for cryogenic cooling of the detector. This continuous wave (CW), frequency-domain instrument is based on a very strong local enhancement of the electro-magnetic field, thus enabling increased coupling of the THz radiation with the sample biomaterials.

The term "Continuous Wave" means tuning THz radiation with very small steps in some spectral range in opposite to a set of separate narrow lines (harmonics) from a laser or other source, and thus one can get the response from the sample in the form of a continuous spectrum.

The disclosed continuous-wave frequency-domain spectroscopic sensor with imaging capability operates at room temperature in the sub-THz spectral region between 315 and 480 GHz. Experimental spectra data is illustrated from biological macromolecules and species obtained using this spectrometer and compare some spectra with simulation results using molecular dynamics. Observed multiple intense and specific resonances in transmission/absorption spectra from nano-gram samples with spectral line widths as small as 0.1 cm-1 provide conditions for reliable discriminative capability, potentially to the level of the strains of the same bacteria, and for monitoring interactions between biomaterials and reagents in near real-time.

Through the correct choice of substrate, concentration of materials in solution or suspension, and material alignment at deposition permitted us to significantly enhance the intensities of modes and the reproducibility of frequencies when using a Fourier transform (FT) Bruker IFS66v spectrometer with a moderate spectral resolution of 0.25 cm-1. Not only were raw transmission spectra measured, it was also possible to extract absorption coefficient data for quantitative characterization of bio-materials.

This enhancement was achieved through the use of the discontinuity edge effect and the extraordinary transmission of a sub-wavelength-slit conductive structure. Observed multiple intense and specific resonances in transmission/absorption spectra from nano-gram samples with spectral line widths as small as 0.1 $cm^{-1}$ provide conditions for reliable discriminative capability, potentially to the level of the strains of the same bacteria, and for monitoring interactions between biomaterials and reagents in near real-time. Only ~20 ng of biomaterial is required as the sample in the present system as compared to the mg sample size required in the previous work done on the Bruker spectrometer. A sealed micro/nanofluidic chip sample holder, in which liquid samples are utilized, the amount of biomaterial required for characterization can be further reduced ~10 to 100 times, thus enabling single biomolecule characterization.

The above provides spectral resolution better than 0.035 cm-1, and significantly improved the detection sensitivity and reliability in the sub-THz operation range as compared to a commercially available spectrometer with a liquid helium cooled detector. Spatial resolution of the instrument is restricted by the opening size of the micro-detector waveguide. Highly resolved transmission (absorption) spectra from only 10-20 ng of biological macromolecules and bacterial cells/spores were demonstrated.

The experimental results measured with high spectral resolution reveal very intense and narrow spectral features from biological molecules and bacteria with widths ~0.1 0.2 cm-1. This corresponds to much longer scattering time values as compared to those previously evaluated using a spectrometer with a resolution of 0.25 cm-1. The narrow width of the spectral features (or small dissipation factor) in the transmission (absorption) spectra in the THz region makes these lines detectable. Thus, a new sub-THz vibrational spectroscopy technology with high spectral and spatial resolution has been developed and experimentally demonstrated in general agreement with modeling results.

The results provide completely new information about the interaction between THz radiation and biological materials, confirming diverse relaxation dynamic mechanisms relevant to sub-THz spectroscopy. This demonstration of multiple intense and specific resonance features provides conditions for reliable discriminative capability of frequency domain spectroscopy to the level of bacterial strains in extremely small sample volumes. Based on the experimental data, an advanced biological sensor, in which the developed spectroscopic instrument is integrated with a microfluidic platform will provide reliable and accurate detection of nanograms of biological materials using optical, highly sensitive biosensors. This new instrument can be used for monitoring interactions between biomaterials and reagents, and for studying conformational change and biomedical processes in near real-time.

4. Statistical Model for *E. coli* DNA Sequence Using Monte-Carlo Technique for Markov Chain Terahertz spectroscopy of biological macromolecules reflects low frequency internal molecular vibrations. While sub-THz radiation can effectively be used to identify various complex biological molecules, a deeper understanding of interaction mechanism of THz radiation with biological molecules has been found to require development of computational modeling in parallel with experimental studies. We have simulated spectra of relatively small biological molecules like transfer RNA or protein thioredoxin from *E. coli* using molecular dynamic (MD) simulations (sections 2 and 3). A rather good correlation of simulated spectra with experimental data was demonstrated. However a large size of macromolecules (~5 million base pairs for *E. coli* DNA) prevents direct application of MD simulation at the current level of computational capabilities. A simplified model of the DNA macro molecule has been developed so that the model would capture the most important low-frequency vibrational characteristics of the native DNA. One way to reach the goal is to build a modeling sequence by using the most frequent repeating fragments (2-10 base pairs) occurring in the original DNA. The constructed models and MD simulations of the modeled sequences enable the calculation of expected absorption spectra, and provides a better understanding of the mechanism of interaction of THz radiation with a biological molecule by analyzing dynamics of atoms and correlation of local vibrations in the modeled molecule.

4.1. Statistical Model for *E. coli* DNA Sequence

The new procedure constructs a short DNA sequence much less than the length of the genome, in order to model a whole bacterial genome. A second order Markov chain framework was combined with a Monte-Carlo technique. The statistical model approach is based on conditional probabilities of occurrence of a single base $X_{i+2}$, given that two previous bases in the sequence are $X_i$ and $X_{i+1}$.

Using Monte-Carlo technique it is possible to find the most probable sequence of a length L, when random sequences of this length are generated using the conditional probabilities mentioned above. The most probable first two bases have to be found directly from the genome. Then the third base can be found as having the greatest occurrence in random sequences, given that first and second ones have already been determined. Forth base can be found the same way, given that first three bases are known. Applying this algorithm iteratively, each base in the sequence can be specified.

An additional condition is applied to every random sequence to be accepted and used in the further analysis:

$$(R_g - \Delta < R_S < R_g R + \Delta), \Delta << R_g, \quad (2)$$

where $R_g$ and $R_S$ are the ratios of the nucleotide of a certain type to the total number of nucleotydes in genome and in the randomly generated sequence, correspondently. $\Delta$ is the tolerance parameter which determines how accurately should be the correspondence between $R_g$ and $R_S$. In this case, $\Delta=0.007$.

*E. coli* bacteria include different strain groups with sequences similarity between strains in one group. Statistical models enable us to find strains, which can be discriminated on the basis of their modeled sequencing resulted in specificity of their vibrational spectroscopic signatures. By generating statistical models for different strains, it can predicted that if some DNA strains have different modeled sequences they may also have different absorption spectra.

*E. coli* strain BL21 (4534552 bp) derived from *E. coli* strain B is commonly used as a host strain for protein expression and purification. The highly virulent strain CFT073 is one of uropathogenic strains of *E. coli*, which is the most common cause of non-hospital-acquired urinary tract infections.

The sequences for two *E. coli* strains, pathogenic CFT073 and non-pathogenic BL21, are quite different:

BL21—GCGCGCAGCATTTTTTTCAGCGCAGC-GAAAAATTTCGCGCGC-AGTTTAAC-GCGATCAGT,
CFT-073—CGCAGCAGCACATTTTTTTTCAGCG-CAGCA-GCAGATTTTCAGCAGATCAGCGATCAGT,
and it can expected that t a noticeable difference in simulated absorption spectra from these two strains.

We have modeled 20, 40 and 60 base sequences for two *E. coli* strains, a non-pathogenic strain BL21 and a pathogenic strain CFT073 Calculated sequences for 20, 40 and 60 bases of a CFT073 *E. coli* strain are compared in the Table 1. Since the proposed modeling approach is used to determine the most frequent pattern in the genome, with increasing the length, the modeled sequence becomes more representative and able to accurately reflect characteristic features of genomic DNA. *E. coli* genome contains large numbers of repeated fragments of different length like TTTTT. The presentation of these fragments in a statistical model is improving with increased model length and the 60 bp sequence would be more accurate.

4.2. Discriminative Capability

Table 2 lists generated DNA 60 bp sequences from models for several *E. coli* strains. By generating statistical models for different strains it can be verified that if some DNA strains have different modeled sequences they may also have different absorption spectra. For the first three strains, K-12 DH10B, K-12 BW2952, and K-12 MG1655, the statistical models are identical as will be their THz spectra simulated on the bases of these models. As a result, it will not be able to discriminate between these strains in modeling of 60 bases. It is also expected that these strains will be more difficult to discriminate experimentally. The sequences for two E. coli strains, pathogenic CFT073 and non-pathogenic BL21, are quite different and a noticeable difference in simulated absorption spectra from these two strains is expected. This is in fact confirmed by the results of MD simulations.

TABLE 1

Modeled 20, 40 and 60 base sequences for CFT073 E. coli strain.

| Model length | Modeled sequence 5'-3' |
|---|---|
| 20 bp | GCAGCATTTCAGCGATCAGT |
| 10 bp | GCGCAGCATTTTTCAGCAGCAGCAGTTTA ACGCGATCAGT |
| 60 bp | GCGCAGCAGCAGCATTTTTTTTCAGCGCAG CAGCAGATTTTCAGCAGATCAGCGATCAGT |

TABLE 2

Comparison of different E. coli strains.

| Strain | Modeled sequence 5'-3' |
|---|---|
| K-12 DH10B | GCGCGCAGCATTTTTTTCAGCAGCAGCAGC AGCAGATTTTTAAACGCGCGATTCAGCGAT |
| K-12 BW2952 | GCGCGCAGCATTTTTTTCAGCAGCAGCAGC AGCAGATTTTTAAACGCGCGATTCAGCGAT |
| K-12 MG1655 | GCGCGCAGCATTTTTTTCAGCAGCAGCAGC AGCAGATTTTTAAACGCGCGATTCAGCGAT |
| K-12 DH1 | GCGCGCAGCATTTTTTTCAGCGCAGCAGAA AAATTTCGCGCGCAGTTTAACGCGATCAGT |
| BL21 | GCGCGCAGCATTTTTTTCAGCGCAGCAGAA AAATTTCGCGCGCAGTTTAACGCGATCAGT |
| B7A | GCGCAGCAGCATTTTTTTCAGCGCAGCAGC AGCAGATTTTTCAGCAGCAGATTCAGCGAT |
| CFT073 | GCGCAGCAGCAGCATTTTTTTCAGCGCAG CAGCAGATTTTCAGCAGATCAGCGATCAGT |
| EDL933 (deadly) | GCGCAGCAGCAGCTGATTTTTTTCAGCAGC AGCAGCATTTTAAACGCGCGTTAACGCAGT |

4.3. Molecular Dynamic Simulation Results 4.3.1. Structure

Using statistical models in MD simulations enables the generations of the structure of DNA strains. When comparing the structure of DNA 60 bp models of two strains in 12 Angstrom water box before and after energy minimization, it has been found that the molecules became more compact after minimization.

4.3.2. Absorption Spectra

Figure 17:
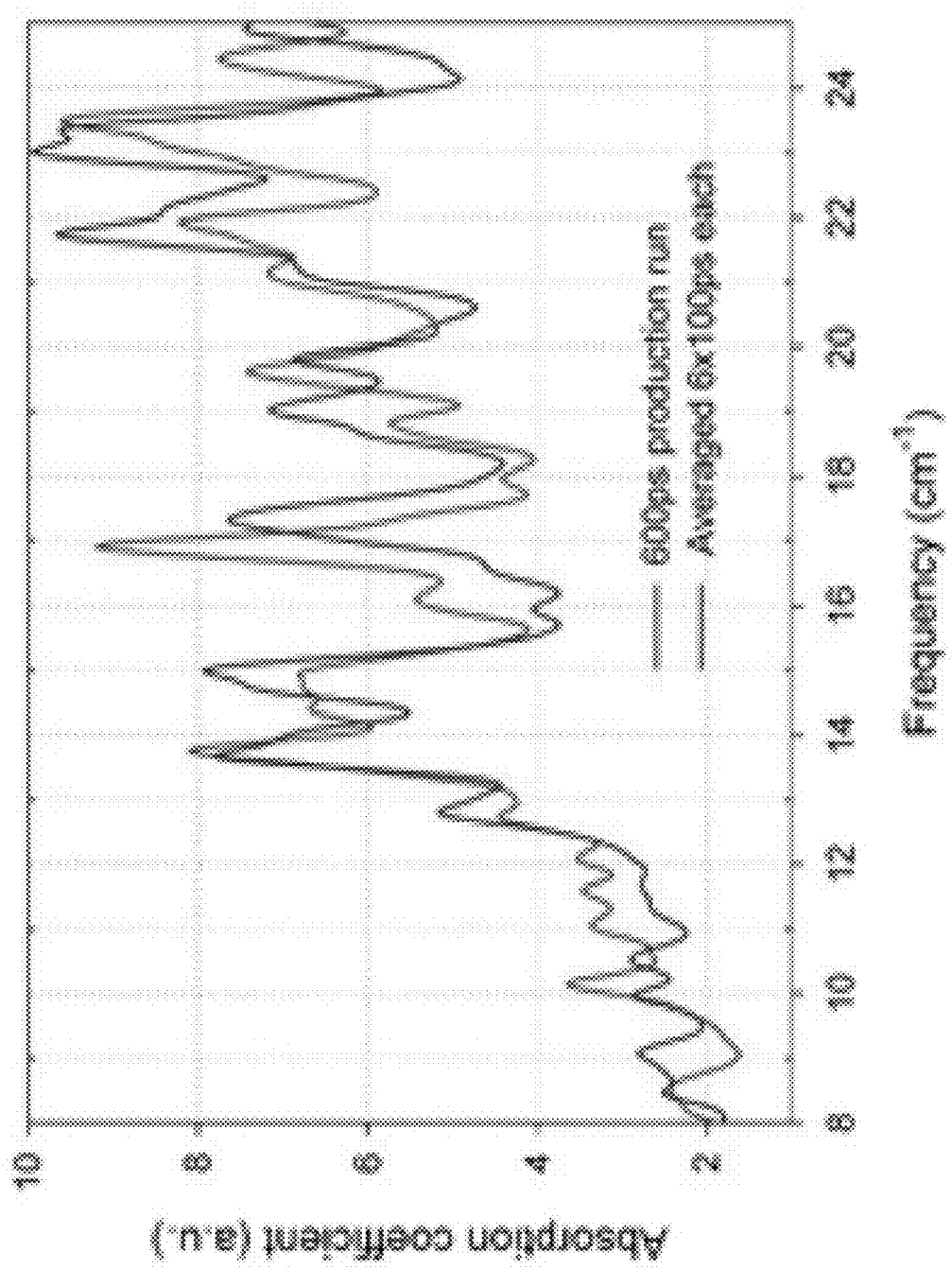

The absorption spectra for 20 60 base model sequences were calculated. MD simulation with explicit water was applied. The convergence of DNA MD simulation was calculated using the approach that was originally developed for E. coli protein thioredoxin to calculate absorption spectra with averaging of atomic displacement correlation matrices. FIG. 17 compares two simulated spectra for 60 bp sequence of CFT073 E. coli strain model presented in Tables 1 and 2. The first spectrum is obtained in a 600 ps production run, and the second one is calculated using averaging correlation matrices procedure for 6×100 ps intervals taken from the same run. The convergence is considered good (results of MD simulations are stable) if only small differences are observed. As it is demonstrated in FIG. 17, the results of MD simulations are stable thus indicating a good convergence of MD simulation for DNA molecules. This result is consistent with the general opinion that convergence problem in MD is less crucial for DNAs compare to proteins.

As expected, spectra are sensitive to the number of base pairs in the model. Models with larger number of base pairs give better presentation of absorption spectrum.

To demonstrate the effect of DNA sequence on their THz vibrational absorption spectra for CFT073 and BL21 was simulated as shown in FIG. 18

The modeling results predict that discrimination can be made between pathogenic and nonpathogenic strains of E. coli 60 bp models using their sub-THz vibrational spectra.

Higher spectral resolution gives even better results. Absorption spectra from non-pathogenic BL21 strain and deadly strain EDL933 using 60 bp models (water box 12 A, averaged in all three directions, dissipation factor 0.12 cm-1) are shown in FIG. 19. Many features for discrimination are available. This spectral resolution is already demonstrated in the range 11-16.8 cm$^{-1}$ using the spectrometer of the present invention.

4.3.3. Effect of Water

When modeling biological molecules in water solutions, complexes of biomaterial with water are generated and studied. In the standard simulation a biomolecule is placed inside a 12 A water box containing more than 30 thousands of water molecules. It is a known fact that the first several layers of water, the mostly close to a bio-molecule, have different 3D structure and properties compare to water layers far away from a solvate. These "internal" layers are tight bonded and can have almost a crystalline structure with large number of hydrogen bonds which might contribute to vibrational spectra.

By modifying one of MD parameters, the size of water box, the variability of THz absorption spectra from bio-molecules can be studied depending on material concentration in water solution and even at transition to dry condition. Experimental absorption spectrum for a virtually dry E. coli B strain produces significantly reduced intensities of peaks.

Figure 15:
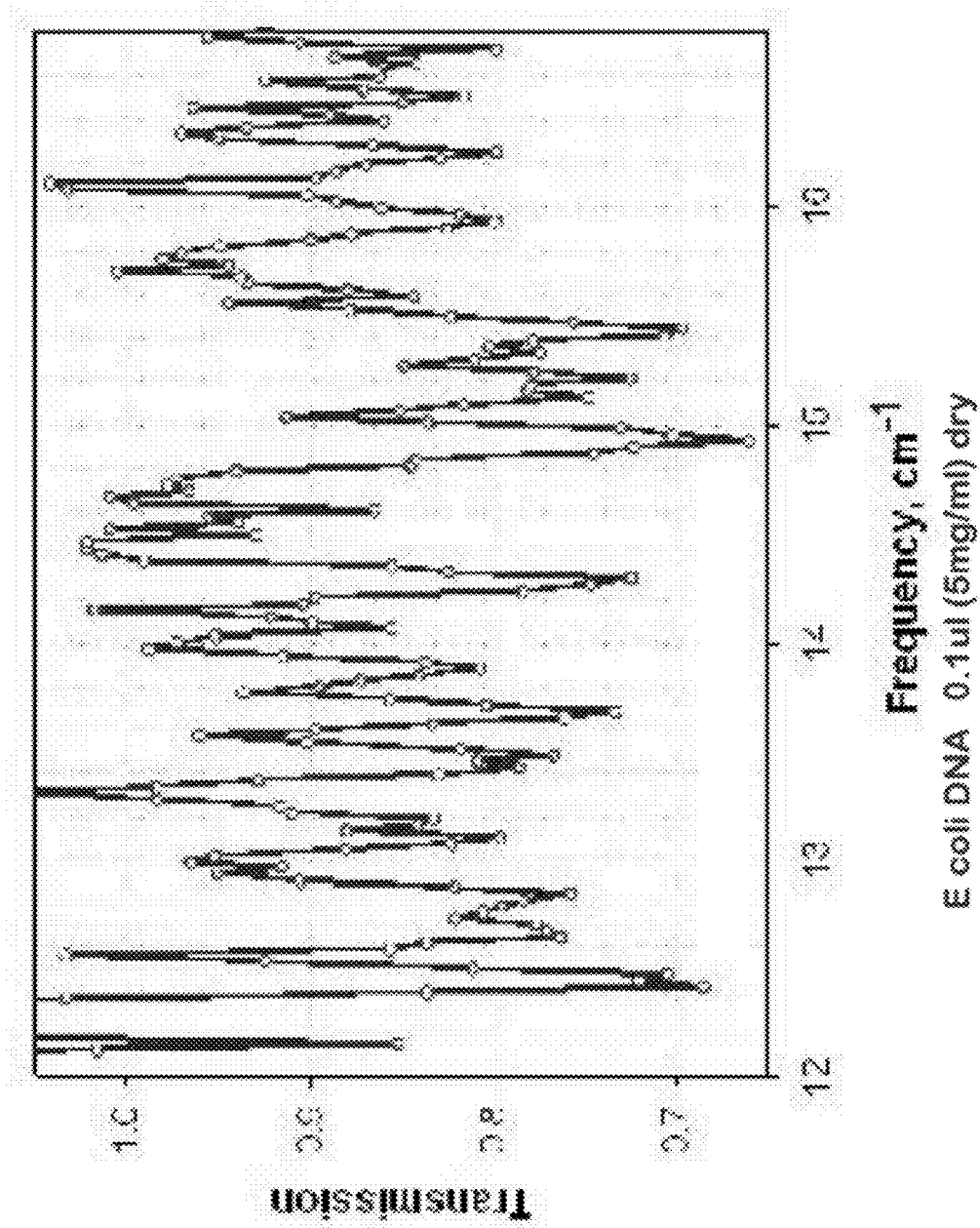
FIGS. 15 and 17 show Transmission and absorption spectra of *E. coli* DNA.
Figure 16:
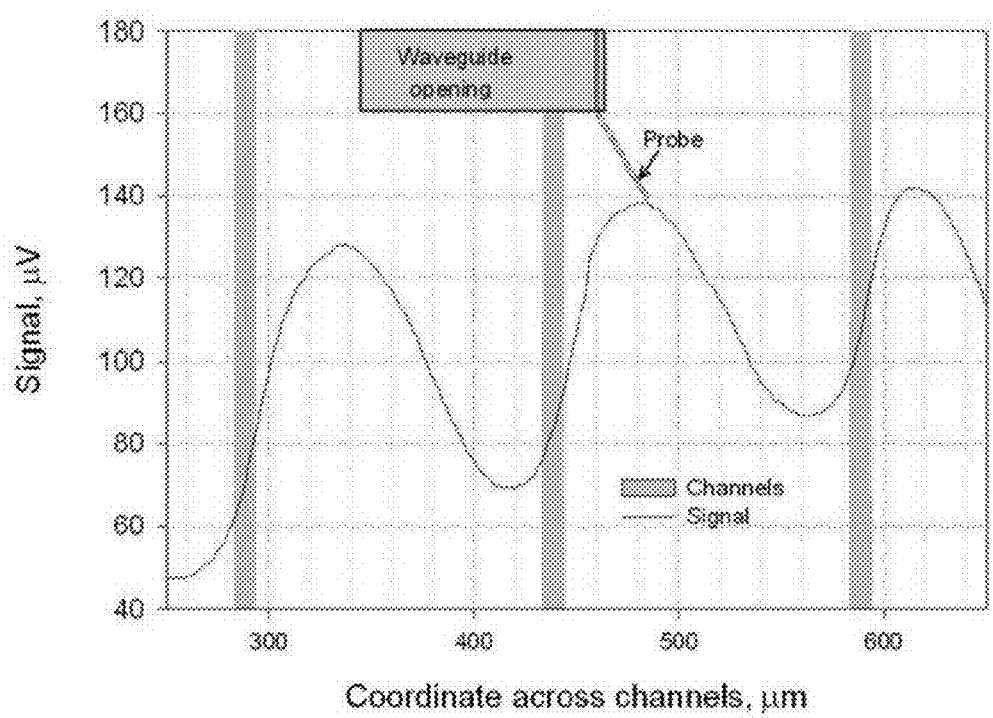
FIG. 16 shows longer scan with transmission close to 1 when the probe is positioned above empty channels, and reduced to about 60% in area with biomaterial in the channels.

4.4. Highly Resolved Vibrational Spectroscopy (0.03 cm$^{-1}$): Comparison with Experiment Sample results from spectroscopy with the resolution of 0.03 cm$^{-1}$. The test results in show the periodicity of the transmitted signal at a frequency of 15.5 cm-1, as the probe scanned across channels of the array structure. It shows the same periodicity as the array itself as expected, although slightly offset in the x direction from the channels. FIG. 16 shows longer scan with transmission close to 1 when the probe is positioned above empty channels, and reduced to about 60% in area with biomaterial in the channels. The actual reduction depends on the amount of biological material present in a channel. Transmission and absorption spectra of E. coli DNA are shown in FIG. 15. Very narrow spectral lines are detected, with a width of ~0.1-0.2 cm-1. The peak positions are preserved in the spectra of samples with different amounts of material, although, the intensities of the absorption peaks calculated per unit mass are often reduced for larger sample amounts. It was assumed that the thickness of the sample material after drying was proportional to its mass, determined from the volume of solution and the concentration of material in solution. This gave us the mass of solid material in the drop after evaporation of water. It was further assumed that the spot area was the same when more material was added. However, currently the spot size cannot be controlled and cannot be sure that this area is the same. This may explain the apparent dependence of absorption coefficient on mass in FIG. 10.

Transmission spectra were obtained in the sub-THz region between 315 and 480 GHz for both, macromolecules and biological species. Due to high sensitivity, good spectral resolution, and spatial resolution below the diffraction limit, this spectroscopic instrument enables us to observe intense and narrow spectral resonances in transmission/absorption spectra of nano-samples from biological materials. To demonstrate the capabilities of the spectrometer, transmission spectra from bacterial cells and some of their molecular components (DNA, thioredoxin) were measured. From the transmission spectrum of *E. coli* DNA shown in FIG. 15, the width of spectral lines can be estimated as ~0.1 $cm^{-1}$. As demonstrated in FIG. 15, spectral lines are sharper in thin samples and have significant broadening and damping of spectral features in bulk samples, probably due to less oriented material. Very thick samples usually do not demonstrate well resolved spectral features in the sub-THz region. This effect can explain the sensitivity of sub-THz spectroscopic characterization to specificities of sample preparation techniques. Further development of the microfluidic sample holder is expected to provide increased reproducibility and efficiency, as the sample presentation in the spectrometer detection region will be more accurate and controlled.

To further confirm the reality of the observed narrow and intense resonance features in the sub-THz transmission/absorption spectra of biological materials as measured with the new spectroscopic sensor, the spectrum from the *E. coli* protein thioredoxin was compared in FIG. 12 with computational modeling results using MD simulations with a damping factor of $\gamma=0.12$ $cm^{-1}$.

Figure 9:
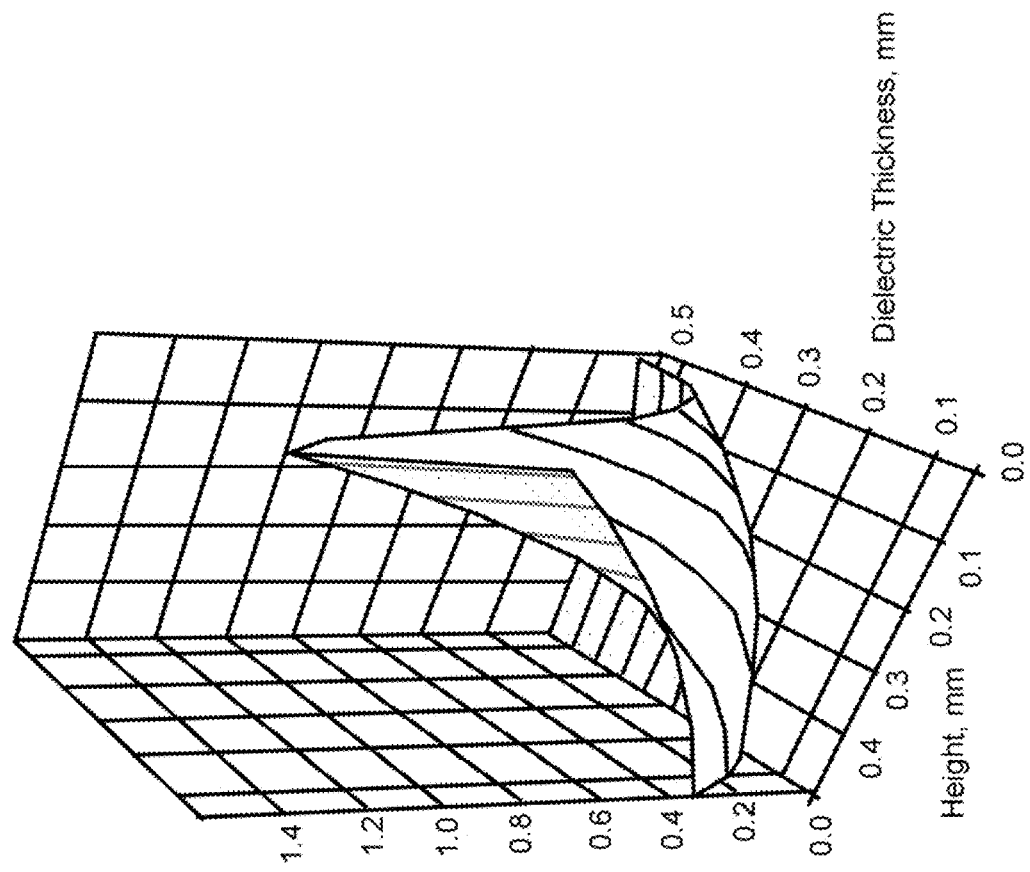
FIG. 9 is a graph illustrating excitation efficiency at 300 GHz using the disclosed spectroscopic sensor in accordance with the present invention.
Figure 10:
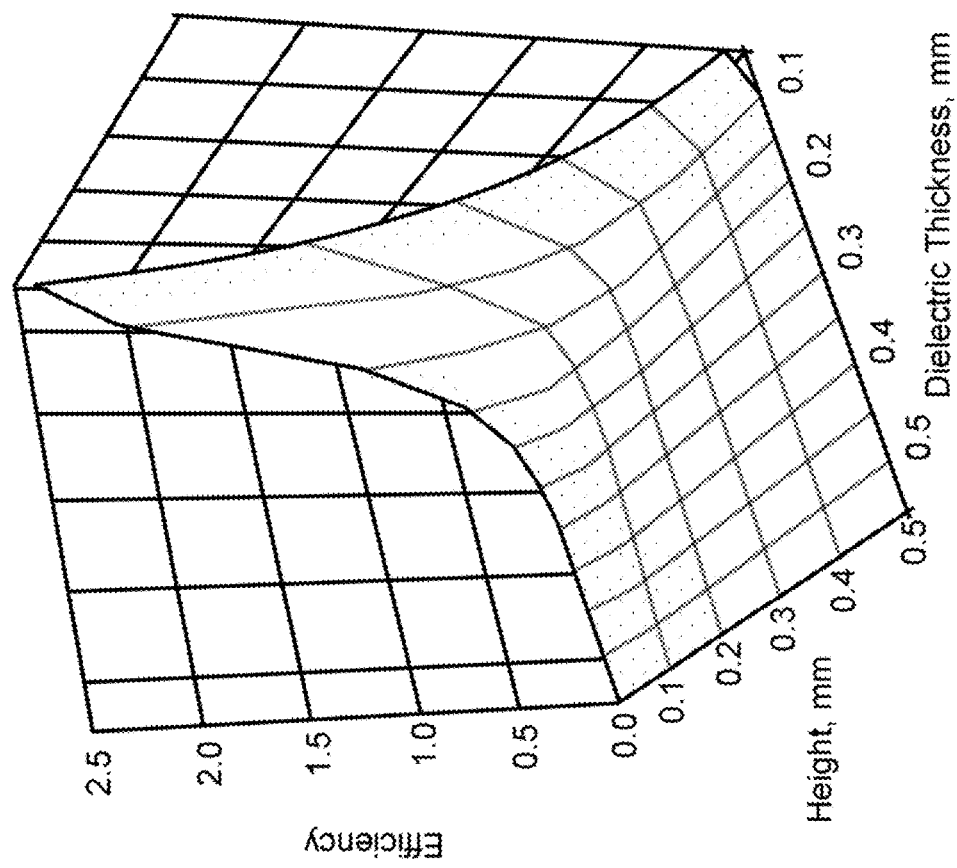
FIG. 10 is a graph illustrating excitation efficiency at 500 GHz using the disclosed spectroscopic sensor in accordance with the present invention.

Due to possible contributions from several different modes occurring at close frequencies, the width of spectral lines gives us an upper limit of $\gamma$. As seen in FIG. 9, not all peaks are reproduced in the measured and simulated spectra, since simulation parameters have not yet been optimized. The same value of $\gamma$ was used to calculate absorption for all vibrational modes; however, the overall correlation between the theory and experimental data confirms again the existence of intense and narrow absorption lines, which can be used for discrimination between different bacteria and strains.

5. Conclusion

A new statistical model was developed to construct DNA sequences significantly less than the length of the entire genome (20 60 base pairs), using the most frequently repeated fragments (2-10 base pairs) in the original DNA. The results were analyzed from MD simulations of the new developed models of DNA sequences from *E. coli*. It has been demonstrated that the application of molecular dynamics simulations to the 60 base pair DNA models provides high discriminative capability for biosensing in sub-THz regime. MD simulation of the chromosomal DNA of select model organisms revealed that in the case of a good spectral resolution discrimination is possible up to the level of strains of one bacterial species. Modeling results are supported by experimental spectroscopic data. The experimental results measured with high spectral resolution demonstrate very intense and narrow spectral features from DNA and a protein thioredoxin from *E. coli* with the line width ~0.1 cm-1. These results combined with MD simulation confirm that highly resolved sub-THz vibrational spectroscopy can be used for reliable and accurate detection of nanograms of *E. coli* using optical, highly sensitive biosensors operating at room temperature with significantly improved ability to discriminate between species up to the level of the strains of the same bacteria.

Cancer

Bone marrow and blood leukemias, account for about 34% of all cancers in children. It is estimated that 48,610 people in the United States will be newly diagnosed with acute lymphoblastic leukemia (ALL) in 2013. ALL is diagnosed in 3000 to 4000 persons in the United States each year, with two-thirds of these being children. Cancers in children often are hard to recognize because the symptoms can overlap with much more common illnesses or injuries. Lab tests used to diagnose and classify leukemia are available including, among others, routine microscopic exams, serum measurement of protein biomarkers, and highly sensitive Polymerase chain reaction (PCR). Most children with acute leukemia have too many white blood cells, however usually the disease cannot be diagnosed without bone marrow tests.

Small sample resonance spectroscopy technology in the sub-Terahertz frequency range as an optical, label-free and reagent-free approach to discover and study potential biomarkers for diagnosis, prognosis, early detection and therapeutically treatment of pediatric ALL cancers would greatly enhance early and accurate diagnosis.

Three Steps are Required:

a) demonstration of unique spectroscopic signatures from markers like DNA, RNA, proteins, and entire cells in specimen from core or fine-needle aspiration biopsy (FNAB) using a spectroscopic sensor having high spectral and special resolution and combined with a microfluidic device, b) spectroscopic evaluation of potential molecular markers in saliva or blood for example, circulating short transfer RNA molecules) in conjunction with standard molecular biology techniques, c) characterization of the sensitivity, variation, reproducibility and accuracy of the method.

Recent advances in sequencing technologies and proteome analysis and associated micro RNA changes have led to an increased focus on blood-derived nucleic acid based approaches for biomarker discovery. Investigations of differences between normal and malignant cells have revealed alterations in DNA, proteins and associated micro RNA changes. Many of these differences have been shown to be detectable in the blood stream. Therefore, there is strong rationale for taking advantage of increasingly available sequencing modalities for blood-derived biomarker discovery. However, these methods are costly and yield terabytes of data requiring significant bioinformatics analysis capabilities. Thus, there is a crucial need for a screening test that is based on ubiquitous nucleic acid or proteins composition differences between normal and malignant cells, and is simple to perform and interpret.

An embodiment of the invention is directed to cancer diagnostic technology using spectroscopic signatures from biological molecules and cells in the sub-terahertz (THz) spectral range as biomarkers, measurable characteristics that reflects the presence and severity of disease state, and the detection of leukemia with the focus on ALL in children. Vibrational resonance spectroscopy in the THz ranges is employed for sensing and fingerprinting biological molecules and cells that is based on specificity of resonance features, fingerprints, observed in absorption (transmission) spectra of biological molecules and entire bacterial cells. THz radiation interacts with the low-frequency internal molecular vibrations involving the weakest hydrogen bonds and other weak interactions by exciting these vibrations. The sub-THz region of absorption spectra (2-30 cm-1) of bio-molecules reveals resonance features that reflect these low frequency molecular motions. This new technique has recently been demonstrated with high spectral and spatial resolution using the spectroscopic microscope (sensor) of the present invention for detection, characterization and discrimination of biological molecules and cells.

THz vibrational spectroscopy can be more effective than standard methods especially when the quantity of sample material is limited. Well resolved THz spectra from biological molecules and organisms are specific to sequencing and a three-dimensional structure, and can be used for their fast characterization and fingerprinting.

The experiments show that cellular components contribute to spectroscopic signature of the entire microorganism. As noted heretofore with respect to bacteria, because of a cell's small size and relatively low absorption coefficient, the THz radiation propagates through an entire object, allowing the genetic material and proteins all contribute to the THz signature of bacteria or spores. It has now been confirmed that observed spectroscopic features from cells are caused by fundamental physical mechanism of interaction between THz radiation and biological macro-molecules. Particularly, the analysis of results indicates that the spectroscopic signatures of microorganisms originate from the combination of low frequency vibrational modes or group of modes at close frequencies (vibrational bands) within molecular components of cells. The obtained results suggest that THz vibrational spectroscopy adds quantitative genetic information to the characteristic signatures of biological objects, increasing characterization accuracy and selectivity when appropriate spectral resolution is used.

The spectral range below 1 THz is especially attractive for practical applications because of low disturbance from liquid water (2.5 order less absorption compare to a far IR) or other solvents, and from water vapor absorption (sensors do not require evacuation or purging with dry nitrogen). A big advantage of THz spectroscopy is that it is an optical method and is nondestructive for living species.

Examples

*E Coli*

Results from Preliminary Study.

It was demonstrated that the application of molecular dynamics simulations to the 60 base pair DNA models promises high discriminative capability for bio-sensing in sub-THz regime. Modeling results are supported by experimental spectroscopic data measured with high spectral resolution, which demonstrated very intense and narrow spectral features from DNA and a protein thioredoxin from *E. coli* with the line width ~0.1 cm$^-$. There are similarities in some spectral features from bacterial cells and these molecules. The experimental results combined with MD simulation confirm that highly resolved sub-THz vibrational spectroscopy can be used for reliable and accurate detection of nanograms of *E. coli* using optical, highly sensitive biosensors operating at room temperature with significantly improved ability to discriminate between species up to the level of the strains of the same bacteria.

Comparative Testing of Ovarian Cancer and Normal Cells

The unique spectroscopic signatures or 'fingerprints' of ovarian cancer cells in cell culture were identified. The highly sensitive technique, which is both label and reagent free, provides high resolution and is capable of detecting and identifying a single cancer cell by interrogation of specific resonances caused by intra-molecular motions within the cell. The oncology implications for this advance affect diagnosis, prognosis, and early detection of cancer cells. The multi-port device expedite testing and development of treatment modalities. With the complete development of a sealed micro or nanofluidic chip sample holder, liquid samples can be utilized, and the amount of biomaterial required for characterization can be further reduced ~10 to 100 times, thus opening the way for single bio-molecule characterization. In addition, the system of the present invention enables detection of signaling molecules circulating in blood, as well as assessing therapeutic responses from cancer cells.

Cancer cells of two different lines S- and E- have been prepared in alcohol at two different concentration—150 cells/ml and 300 cells/ml and stored at −20 C before measurements. The intensity of radiation passed through the empty channels (without sample material) was measured as a function of frequency before sample material was put on the holder. These measurements were repeated for different channels and at different points along the particular channel, and the results were used as background spectra. The measurements were repeated with sample material in the same channels and at the same coordinate along the channels. Transmission (T) was calculated as ratio of the signal spectrum (with material) to the background spectrum. Transmission was recalculated for absorbance using $A=-\log(T)$ for further comparison with the computational modeling results and analysis. Testing includes reproducibility of results from material in different channels as well as at different positions along the channel.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

THE FOLLOWING REFERENCES ARE
INCORPORATED HEREIN AS THOUGH
RECITED IN FULL

1—Highly Resolved Sub-Terahertz Vibrational Spectroscopy of Biological Macromolecules and Cells, Tatiana Globus, et al IEEE SENSORS JOURNAL, VOL. 13, NO, 1, JANUARY 2013

2—Teraherz vibrational spectroscopy of *E. coli* and molecular constituents: Computational modeling and experiment Tatiana Globus, et al., Advances in Bioscience and Biotechnology, 2013, 4, 493-503 ABB doi:10.4236/abb.2013.43A065 Published Online March 2013.

What is claimed is:

1. A method comprising:
causing a sample to be analyzed via a frequency domain spectroscopy system, said frequency domain spectroscopy system constructed to expose said sample to radiation, in a spectral range of 120-1200 GHz or 4-40 $cm^{-1}$, to detect and identify specific biological or organic chemical materials within said sample, based on narrow, 0.05-0.2 $cm^{-1}$, absorption lines for said sample.

2. The method of claim 1 wherein:
said frequency domain spectroscopy system comprises:
an electronically tunable GHz frequency radiation source with a spectral resolution of at least about 1 GHz;
a sample holder that is substantially transparent to GHz radiation;
a detector incorporating a diode, a circuit, and a probe, said detector constructed to detect radiation passing through said sample; and
a positioning system constructed to position said sample relative to said radiation source and said probe with an accuracy better than 1 µm.

3. The method of claim 1 wherein:
said sample is:
placed in a sample holder;
positioned within an interrogation area of said frequency domain spectroscopy system; and
analyzed via measurements taken by said frequency domain spectroscopy system.

4. The method of claim 1, wherein:
said frequency domain spectroscopy system comprises a detection probe having a dimension in one direction of less than 5 µm.

5. The method of claim 1, wherein:
said frequency domain spectroscopy system comprises a detector, said detector comprising a probe positioned in a near-field region of said sample, said probe constructed to monitor electromagnetic radiation passing through said sample.

6. The method of claim 1, wherein:
interaction of said radiation with said sample is enhanced through use of at least one of a waveguide (strip-line, transmission line or fiber-optic) or a coupling device (accepting antenna) transmitting said radiation from a source to a holder of said sample.

7. The method of claim 1, wherein:
interaction of said radiation with said sample is enhanced through said use of extraordinary transmission and discontinuity edge effects in a holder of said sample.

8. The method of claim 1, wherein:
said frequency domain spectroscopy system is constructed to utilize either scanning of a set sub-range within said spectral range, or interrogation of said sample at specific GHz frequencies selected for identification of each material.

9. The method of claim 1, wherein:
identification of materials is based on comparison with previous experimentally determined absorption spectra, or with computationally modeled spectra in said spectral range.

10. The method of claim 1, wherein:
said frequency domain spectroscopy system is applied to detection and identification of specific bacterial cells in said sample through analytical measurement of unique and distinguishable spectroscopic features in said spectral range.

11. The method of claim 1, wherein:
said frequency domain spectroscopy system is applied to detection and identification of specific viral particles or viral DNA present in said sample through analytical measurement of unique and distinguishable spectroscopic features in said spectral range.

12. The method of claim 1, wherein:
said frequency domain spectroscopy system is applied to detection and identification of specific mammalian cells and their molecular components in said sample, such as cancer cells, through analytical measurement of unique and distinguishable spectroscopic features in said spectral range.

13. The method of claim 1 wherein:
said frequency domain spectroscopy system is applied to specific biomolecules, including proteins and nucleic acids, present in said sample through analytical measurement of unique and distinguishable spectroscopic features in said spectral range.

14. The method of claim 1 wherein:
said frequency domain spectroscopy system is used to identify specific conformations of biomolecules based on analytical measurement of unique and distinguishable spectroscopic features in said spectral range.

15. The method of claim 1 wherein:
said frequency domain spectroscopy system is applied to specific biomolecules, including cell free nucleic acids, present in human body liquids through analytical measurement of unique and distinguishable spectroscopic features in said spectral range.

16. The method of claim 1 wherein:
said frequency domain spectroscopy system is applied to detection of organic chemical compounds in said sample through analytical measurement of unique and distinguishable spectroscopic features in said spectral range.

* * * * *